United States Patent
Perez et al.

(10) Patent No.: US 7,041,085 B2
(45) Date of Patent: *May 9, 2006

(54) DISPOSABLE SELF-SHIELDING UNIT DOSE SYRINGE GUARD

(75) Inventors: Anthony R. Perez, Pasadena, CA (US); John R. Firth, Wilsonville, OR (US); David W. Mitchell, Orange, CA (US)

(73) Assignee: Safety Syrines, Inc., Carlsbad, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 10/023,587

(22) Filed: Dec. 17, 2001

(65) Prior Publication Data

US 2002/0045864 A1  Apr. 18, 2002

Related U.S. Application Data

(63) Continuation of application No. 09/634,689, filed on Aug. 8, 2000, now Pat. No. 6,344,032, which is a continuation of application No. 08/942,938, filed on Oct. 2, 1997, now Pat. No. 6,159,184, which is a continuation-in-part of application No. 08/814,199, filed on Mar. 10, 1997, now Pat. No. 6,171,283.

(51) Int. Cl.
*A61M 5/32* (2006.01)
*A61M 5/00* (2006.01)

(52) U.S. Cl. .................... 604/198; 604/110

(58) Field of Classification Search ............ 604/110, 604/111, 181, 187, 192, 197, 232, 234, 218, 604/263, 198; 128/919

See application file for complete search history.

(56) References Cited

U.S. PATENT DOCUMENTS 2,571,653 A   10/1951   Bastien
3,885,562 A    5/1975   Lampkin (Continued)

FOREIGN PATENT DOCUMENTS

EP   0 405 039 A1    1/1991
EP   0 966 983 A1   12/1999

(Continued)

OTHER PUBLICATIONS

PCT Publication No. Wo 95 04565 A (Safety Syringes, Inc.) Feb. 16, 1995.

(Continued)

*Primary Examiner*—Michael J. Hayes
(74) *Attorney, Agent, or Firm*—Orrick, Herrington & Sutcliffe LLP

(57) ABSTRACT

An improved guard for a medical cartridge, such as a unit dose pre-filled glass syringe, comprising a body for receiving the cartridge, and a shield slidably attached to the body which are pre-assembled and ready to receive a cartridge therein. The body has a locking mechanism on a proximal end thereof which holds the cartridge therein. The body and shield have cooperating detents and detent pockets which allow the shield to be directed distally, from an unguarded position in which the needle on the cartridge is uncovered for delivery of medication, to a guarded position in which the needle is permanently covered for disposal. The body may also include a substantially rectangular-shaped finger grip on its proximal end for receiving a similarly shaped proximal flange on the cartridge, whereby the cartridge is received in a predetermined orientation.

8 Claims, 30 Drawing Sheets

U.S. PATENT DOCUMENTS

| | | | |
|---|---|---|---|
| 3,973,554 | A | 8/1976 | Tipton |
| 4,048,997 | A | 9/1977 | Raghavachari et al. |
| 4,540,405 | A | 9/1985 | Miller et al. |
| 4,573,976 | A | 3/1986 | Sampson et al. |
| 4,631,057 | A | 12/1986 | Mitchell |
| 4,655,751 | A | 4/1987 | Harbaugh |
| 4,681,567 | A | 7/1987 | Masters et al. |
| 4,702,738 | A | 10/1987 | Spencer |
| 4,723,943 | A | 2/1988 | Spencer |
| 4,737,144 | A | 4/1988 | Choksi |
| 4,738,663 | A | 4/1988 | Bogan |
| 4,772,272 | A | 9/1988 | McFarland |
| 4,850,994 | A | 7/1989 | Zerbst et al. |
| 4,874,384 | A | 10/1989 | Nunez |
| 4,917,673 | A | 4/1990 | Coplin |
| 4,923,445 | A | 5/1990 | Ryan |
| 4,927,416 | A | 5/1990 | Tomkiel |
| 4,969,877 | A | 11/1990 | Kornberg |
| 5,000,744 | A | 3/1991 | Hoffman et al. |
| 5,002,537 | A | 3/1991 | Hoffman et al. |
| 5,013,301 | A | 5/1991 | Marotta, Jr. et al. |
| 5,059,185 | A | 10/1991 | Ryan |
| 5,067,945 | A | 11/1991 | Ryan et al. |
| 5,098,382 | A | 3/1992 | Huber et al. |
| 5,108,378 | A | 4/1992 | Firth et al. |
| 5,201,720 | A | 4/1993 | Borgia et al. |
| 5,215,535 | A | 6/1993 | Gettig et al. |
| 5,242,416 | A | 9/1993 | Hutson |
| 5,246,011 | A | 9/1993 | Caillouette |
| 5,269,766 | A | 12/1993 | Haber et al. |
| 5,279,581 | A | 1/1994 | Firth et al. |
| 5,336,185 | A | 8/1994 | Lynch et al. |
| 5,342,320 | A | 8/1994 | Cameron |
| 5,344,407 | A | 9/1994 | Ryan |
| 5,385,557 | A | 1/1995 | Thompson |
| 5,417,660 | A | 5/1995 | Martin |
| 5,433,712 | A | 7/1995 | Stiles et al. |
| 5,437,647 | A | 8/1995 | Firth et al. |
| 5,445,620 | A | 8/1995 | Haber et al. |
| 5,492,536 | A | 2/1996 | Mascia |
| 5,498,244 | A | 3/1996 | Eck |
| 5,514,107 | A | 5/1996 | Haber et al. |
| 5,522,812 | A | 6/1996 | Talon |
| 5,562,626 | A | 10/1996 | Sanpietro |
| 5,569,211 | A | 10/1996 | Lekhgolts et al. |
| 5,573,512 | A | 11/1996 | Van Den Haak |
| 5,624,400 | A | 4/1997 | Firth |
| 5,674,203 | A | 10/1997 | Lewandowski |
| 5,855,839 | A | 1/1999 | Brunel |
| 6,159,184 | A * | 12/2000 | Perez et al. ................ 604/192 |
| 6,171,283 | B1 * | 1/2001 | Perez et al. ................ 604/192 |
| 6,186,980 | B1 | 2/2001 | Brunel |
| 6,193,695 | B1 | 2/2001 | Rippstein, Jr. |
| 6,319,233 | B1 | 11/2001 | Jansen et al. |
| 6,344,032 | B1 * | 2/2002 | Perez et al. ................ 604/198 |

FOREIGN PATENT DOCUMENTS

| | | |
|---|---|---|
| FR | 2 654 346 A1 | 5/1991 |
| FR | 2782011 | 8/1998 |
| FR | 2782012 | 8/1998 |
| FR | 2 764 195 A1 | 12/1998 |
| FR | 2788984 | 1/1999 |
| FR | 2788985 | 7/1999 |
| FR | 2 778 853 A1 | 11/1999 |
| FR | 2788986 | 11/1999 |
| FR | 2788983 | 1/2000 |
| FR | 2 799 976 A1 | 4/2001 |
| GB | 2283425 | 5/1995 |
| WO | WO 88/02297 A1 | 4/1988 |
| WO | WO 99/17823 A1 | 4/1999 |
| WO | WO 01/41841 A2 | 6/2001 |
| WO | 2 801 795 A1 | 6/2001 |

OTHER PUBLICATIONS

PCT Publication No. EP 0 740 942 A Brunel ,(Sanofi) Nov. 6, 1996.
PCT Publication No. EP 0 864 335 A (Safety Syringes, Inc.) Sep. 16, 1998.
U.S. Patent and Trademark Office, Official Gazette, vol. 1223, No. 2, pp. 818, 819, and 820, dated Jun. 8, 1999.
U.S. Patent and Trademark Office, Official Gazette, vol. 1223, No. 4, pp. 2156, 2157, and 2575, dated Jun. 22, 1999.
U.S. Patent and Trademark Office, Official Gazette, vol. 1224, No. 1, pp. 303, 305, and 306, dated Jul. 6, 1999.
U.S. Patent and Trademark Office, Official Gazette, vol. 1224, No. 4, pp. 3115 and 3404, dated Jul. 27, 1999.
U.S. Patent and Trademark Office, Official Gazette, vol. 1232, No. 1, pp. 381, 382, 384, 385, 386, and 387, dated Mar. 7, 2000.
U.S. Patent and Trademark Office, Official Gazette, vol. 1232, No. 2, pp. 1507, 1508, and 1509, dated Mar. 14, 2000.
U.S. Patent and Trademark Office, Official Gazette, vol. 1232, No. 3, p. 2532, dated Mar. 21, 2000 Book 2 of 2 Books.
U.S. Patent and Trademark Office, Official Gazette, vol. 1232, No. 4, p. 3505, dated Mar. 28, 2000.
U.S. Patent and Trademark Office, Official Gazette, vol. 1234, No. 4, pp. 3543 and 3829, dated May 23, 2000.
U.S. Patent and Trademark Office, Official Gazette, vol. 1235, No. 2, pp. 1234, 1443, and 1444, dated Jun. 13, 2000.
U.S. Patent and Trademark Office, Official Gazette, vol. 1235, No. 3, pp. 2456 and 2457, dated Jun. 20, 2000.
U.S. Patent and Trademark Office, Official Gazette, vol. 1236, No. 1, p. 443, dated Jul. 4, 2000.
U.S. Patent and Trademark Office, Official Gazette, vol. 1236, No. 2, pp. 1625 and 1626, dated Jul. 11, 2000.
U.S. Patent and Trademark Office, Official Gazette, vol. 1236, No. 3, pp. 2873 and 2874, dated Jul. 18, 2000.
U.S. Patent and Trademark Office, Official Gazette, vol. 1236, No. 4, pp. 3963 and 3964, dated Jul. 25, 2000.
U.S. Patent and Trademark Office, Official Gazette, vol. 1237, No. 1, pp. 435 and 436, dated Aug. 1, 2000.
U.S. Patent and Trademark Office, Official Gazette, vol. 1237, No. 2, pp. 1669 and 1670, dated Aug. 8, 2000.
U.S. Patent and Trademark Office, Official Gazette, vol. 1237, No. 3, pp. 2845 and 2846, dated Aug. 15, 2000.
FR Abreges Du Contenu Technique De L'Invention, 00/14, A61L p. 28.
FR Abreges Du Contenu Technique De L'Invention, 00/14, A61M p. 29.
FR Abreges Du Contenu Technique De L'Invention, 00/06, A61M p. 31.
FR Abreges Du Contenu Technique De L'Invention, 00/13, A61M p. 36.
FR Abreges Du Contenu Technique De L'Invention, 00/25, A61M p. 39.
FR Abreges Du Contenu Technique De L'Invention, 00/31, A61M p. 40.
FR Abreges Du Contenu Technique De L'Invention, 00/31, A61M p. 41.
FR Abreges Du Contenu Technique De L'Invention, 00/26, A61M p. 43.
FR Abreges Du Contenu Technique De L'Invention, 99/25, A61M p. 49.

* cited by examiner

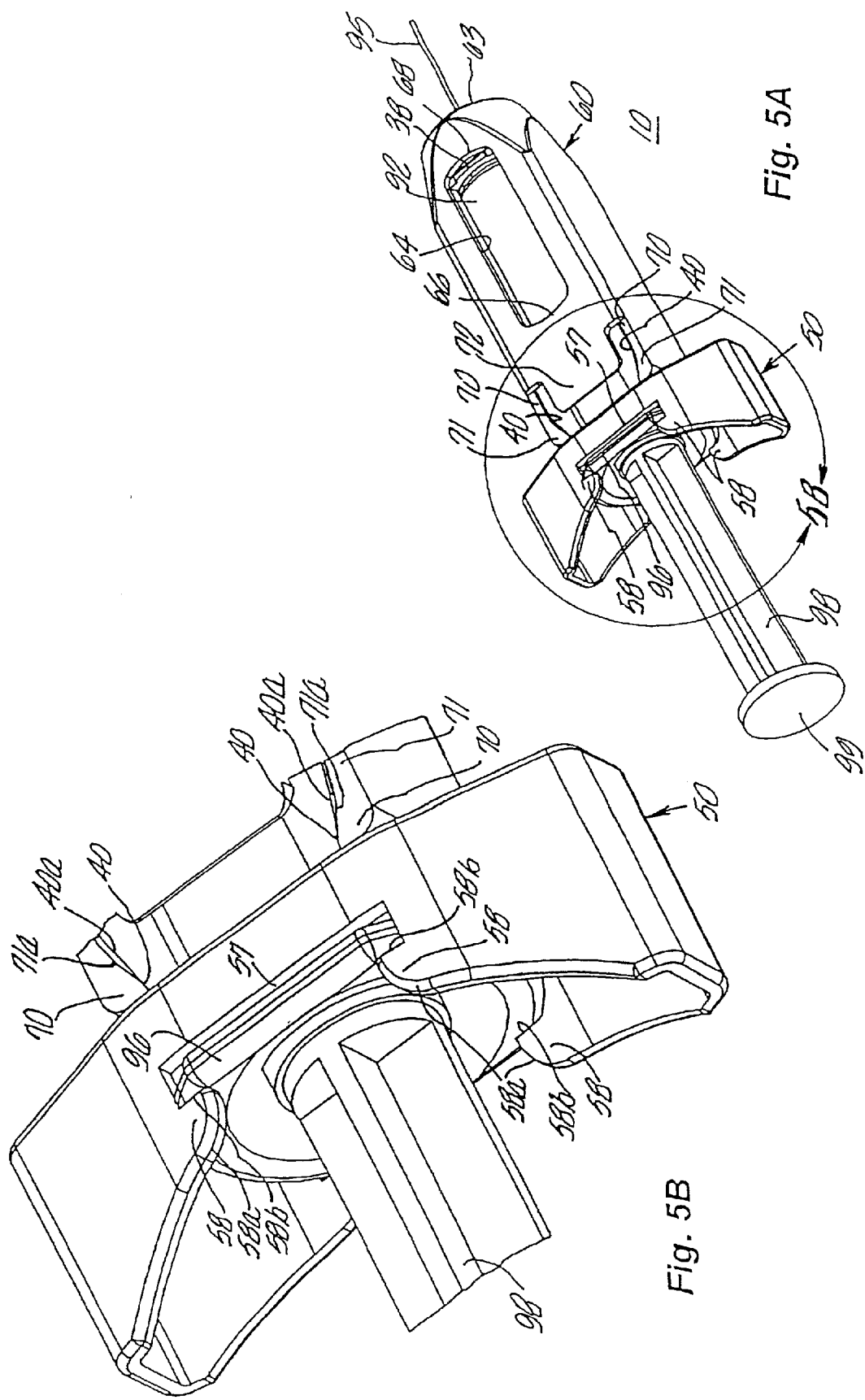

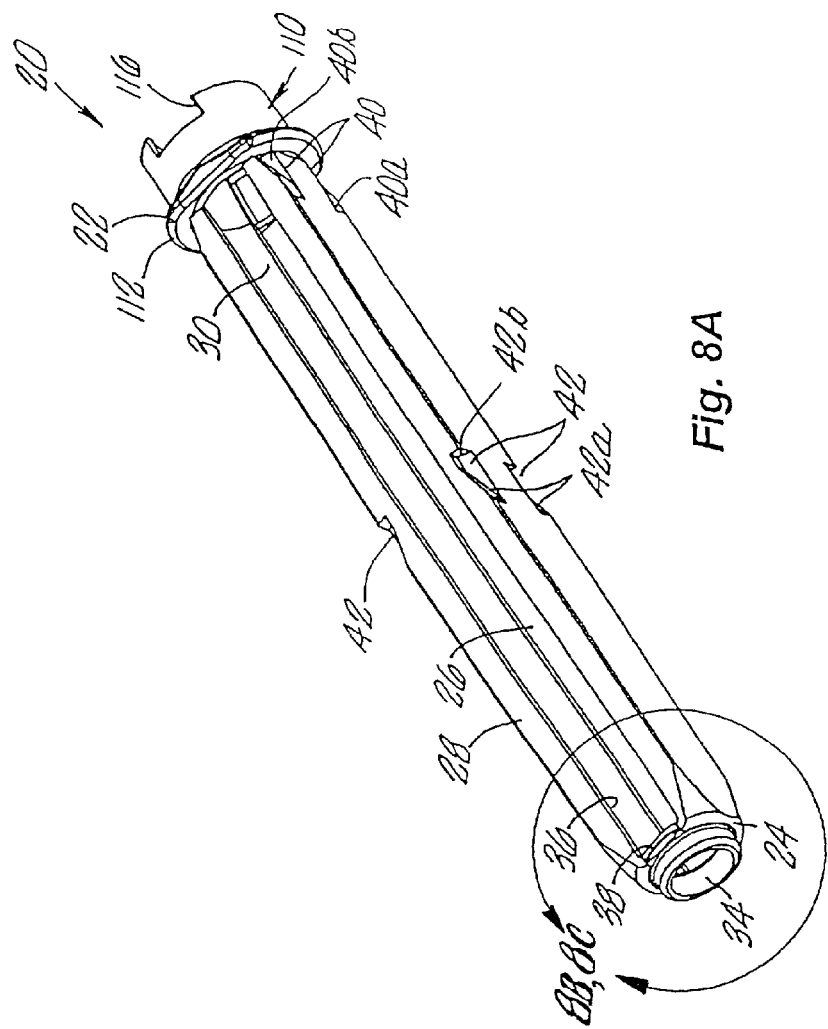
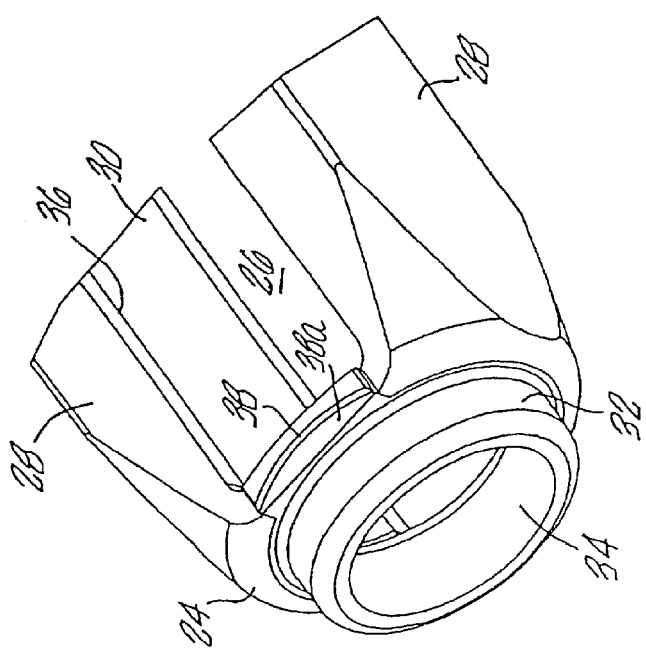
Fig. 8A
Fig. 8B

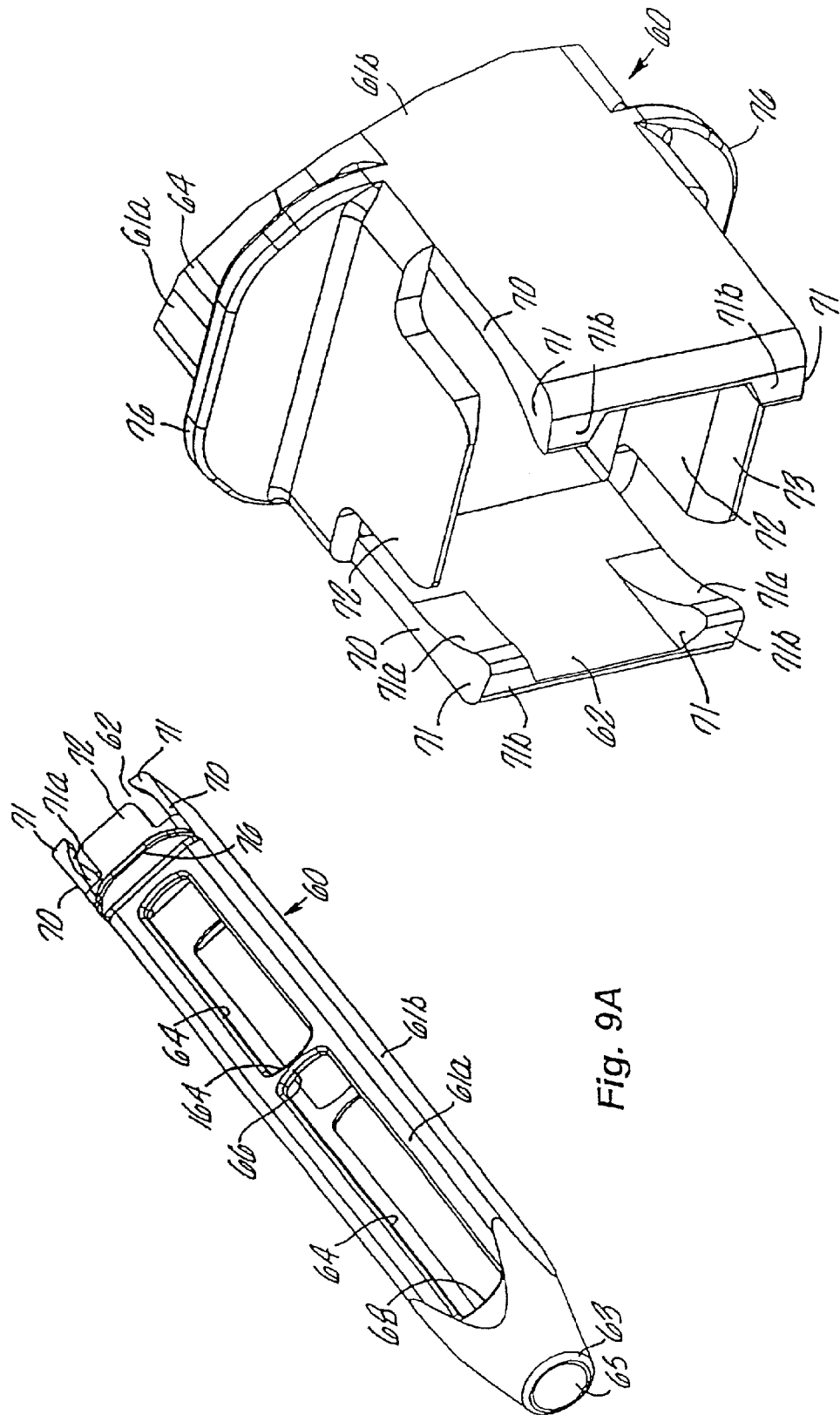

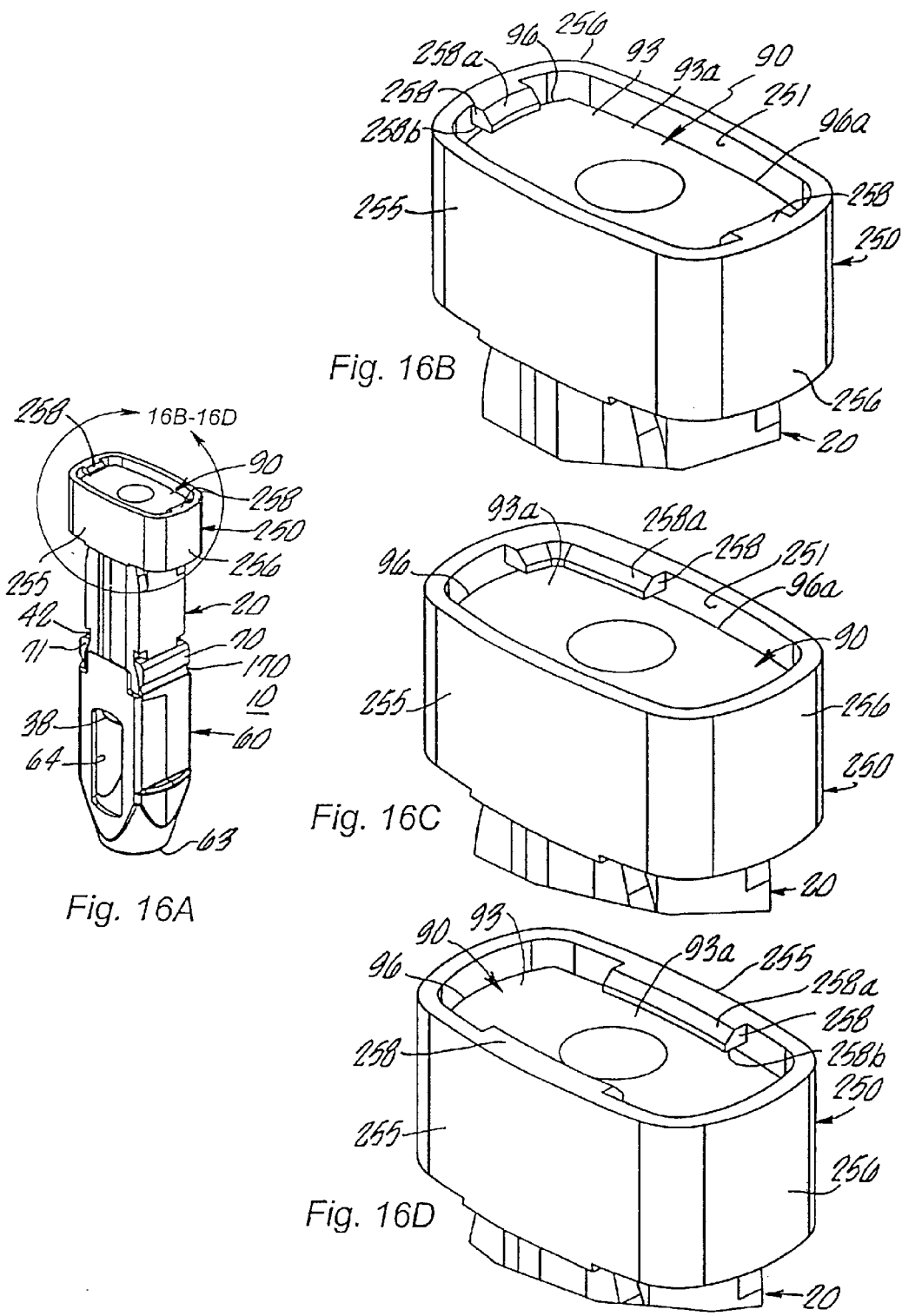

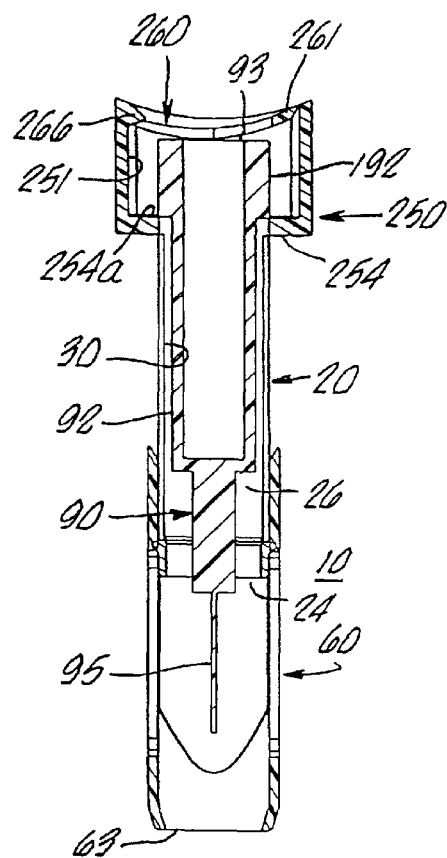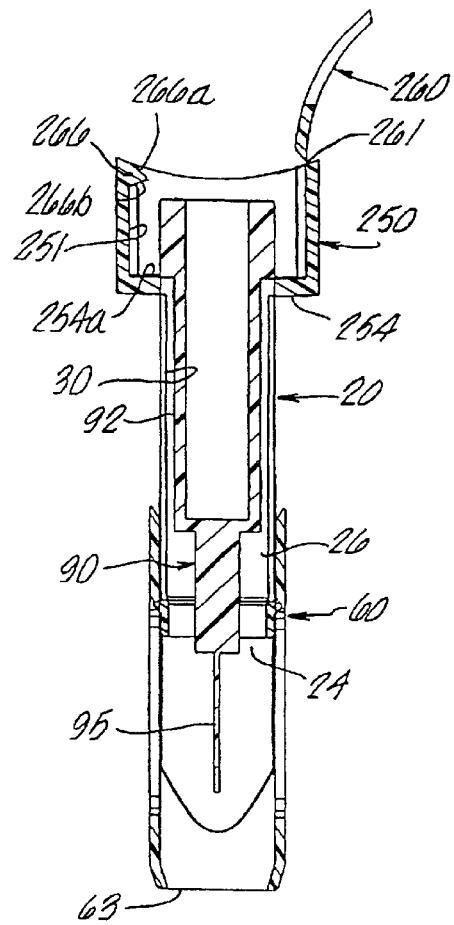
Fig. 17C
Fig. 17D
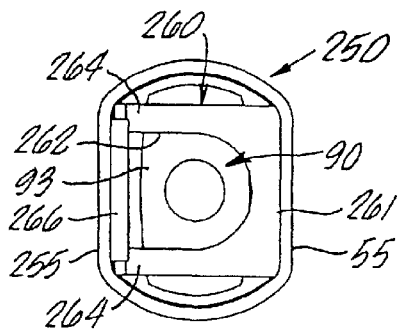
Fig. 17E

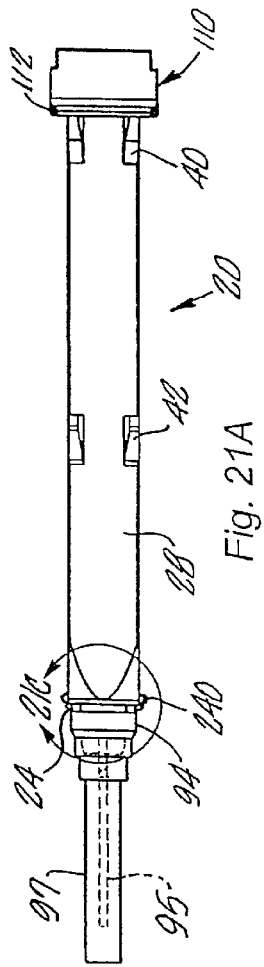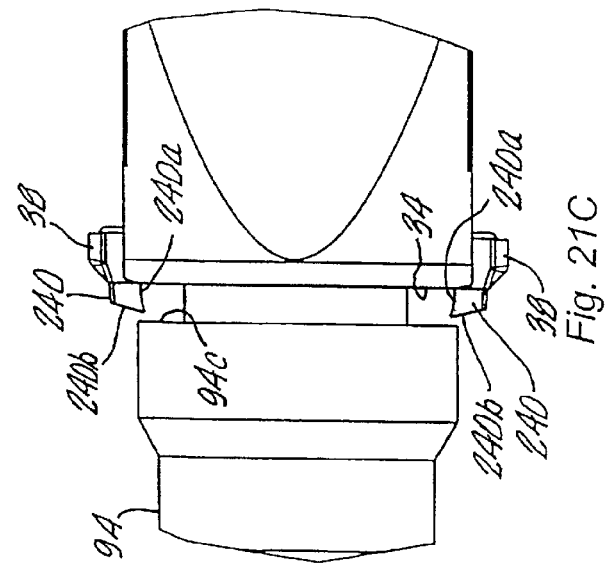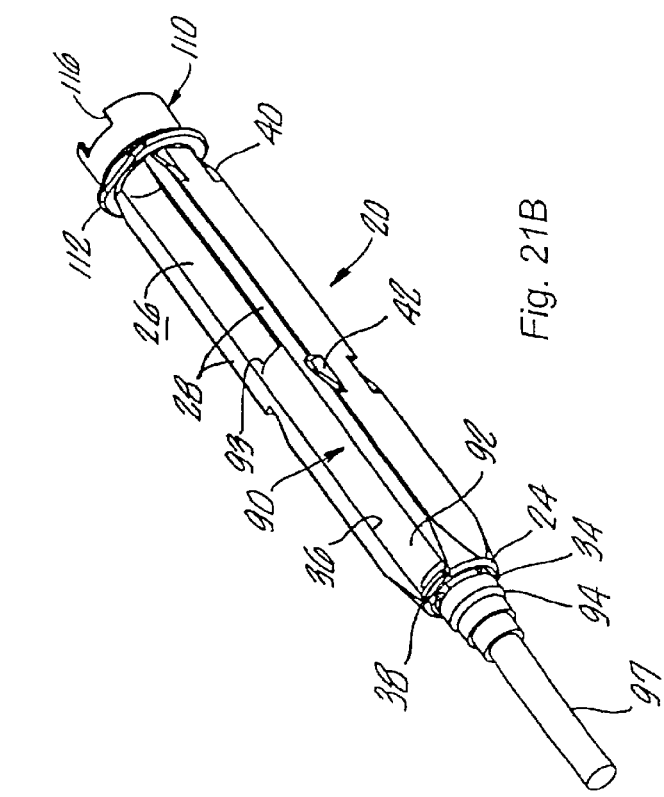
Fig. 21A
Fig. 21B
Fig. 21C

DISPOSABLE SELF-SHIELDING UNIT DOSE SYRINGE GUARD

This application is a continuation of application Ser. No. 09/634,689 now U.S. Pat. No. 6,344,032, filed Aug. 8, 2000, which is a continuation of application Ser. No. 08/942,938 filed on Oct. 2, 1997, issued as U.S. Pat. No. 6,159,184, which is a continuation-in-part of application Ser. No. 08/814,199, filed Mar. 10, 1997, issued as U.S. Pat. No. 6,171,283.

FIELD OF THE INVENTION

The present invention relates generally to syringes, and more particularly to an improved syringe guard for a unit dose cartridge or pre-filled syringe and including a shield for covering the needle thereof after medication is dispensed from the syringe.

BACKGROUND

Medication is often dispensed using a unit dose medical cartridge, such as an ampule, vial or syringe, and a syringe holder, injector or adapter. The cartridge typically has a barrel with a needle at one end and a plunger at the other end. Such cartridges are often referred to as "pre-filled syringes" because they contain a specific dosage or volume of medication when they are initially provided, as compared to conventional syringes which are furnished empty and filled by the user prior to use. Alternatively, the medical cartridge may include a rubber stopper instead of a needle, or may include a piston rather than a plunger on the other end. The syringe adapter is typically a hollow body adapted to hold the cartridge, including a plunger to engage and move the piston in the cartridge.

Because of the threat of communicable diseases, a number of syringes and adapters have been developed to prevent accidental needle sticks or inadvertent reuse of needle devices. Many of these devices, however, are not easy to use or are complicated to manufacture, resulting in less effective disposable syringe devices.

For example, U.S. Pat. No. 5,569,211 discloses a syringe that allows the needle of the syringe to be withdrawn into the barrel of the syringe after medication is dispensed from it. This device, however, is a specially designed substitute for a conventional syringe, and cannot be used to hold commercially available pre-filled syringes.

U.S. Pat. No. 5,522,812 discloses a complicated syringe shield device for holding a conventional cartridge not having its own needle. The device has a number of complicated parts, including a cylindrical body, a double needle assembly, a cylindrical shield, a special collar piece allowing the shield to be drawn over the needle and locked, and a plunger assembly, resulting in a device that is potentially difficult and expensive to manufacture. The device also requires two hands to operate, one to hold the body, and one to rotate the shield into the locked position, which may be inconvenient to the medical professional using the device.

Another consideration with unit dose cartridges and pre-filled syringes is that they are often made from glass, particularly for holding certain vaccines or biotech drugs where concern about micro-organisms or other contaminants is most in critical. Glass cartridges and pre-filled syringes are very fragile and often break during transportation or use. Some existing adapters may not adequately protect the syringe contained therein from such risks. Others provide greater protection for the cartridge, but may obstruct the professional's view of the syringe when the device is being used, hampering monitoring of the medication being delivered.

Therefore, there is a need for an improved safety syringe which is inexpensive and simple to manufacture.

In addition, there is a need for a safety syringe guarding mechanism which provides improved protection for the cartridge or pre-filled syringe therein, but allows effective observation of the syringe and the medication being dispensed.

SUMMARY OF THE INVENTION

The present invention is directed to a guard or adapter for a medical cartridge, such as a unit dose cartridge or pre-filled syringe, that is used to inject medication or other drugs into a patient. Generally, the guard comprises two parts, namely a housing or body for receiving and holding the cartridge, and a protective case or shield slidably attached to the body. In addition, for a cartridge provided without its own plunger, an embodiment of the guard includes a finger grip plug that is attached to the body and a plunger connectable to the piston of the cartridge. The various parts are generally molded from a suitable plastic, such as polypropylene, K-Resin® (a synthetic resinous polymer of butadiene and styrene), or polycarbonate, having a clear finish.

The body generally includes two elongate rails or similar structures defining a substantially rectangular shape, having a cavity therein adapted to receive a medical cartridge or a pre-filled syringe. The body has an open proximal end communicating with the cavity, a distal end with an opening through it, and possibly a collar molded to the distal end. The body may also include a plurality of tabs or ribs extending along a portion of the cavity adapted to engage the barrel of a cartridge received therein.

The protective case or shield is a tubular member adapted to slidably fit on the body, having open proximal and distal ends. One or more elongate windows are formed in the shield, allowing observation of the cartridge or pre-filled syringe held within the body. One or more windows, preferably the same windows used for viewing the cartridge, also cooperate with a stop tab or tabs molded on the body, thereby limiting the relative sliding relationship of the shield and the body. In addition, the shield includes a set of detents, preferably comprising a pair of detent arms and protruding detents molded into the proximal end of the shield. The detents cooperate with one or more sets of detent pockets molded into the body to lock the shield in relation to the body.

The shield is generally provided pre-assembled on the body, preferably by inserting the body into the shield until the stop tabs on the body communicate with the elongate windows on the shield. The shield may then slide in relation to the body between a proximal or unguarded position and a distal or guarded position, defined by the length of the windows in the shield. The guard is generally provided with the shield in the proximal or unguarded position, wherein the stop tabs abut the distal edges of the windows. Alternatively, the proximal travel of the shield may be limited by the detent arms abutting a finger grip on the body. In the unguarded position, the detents on the shield preferably engage a set of proximal detent pockets on the body, holding the shield in relation to the body.

Generally, after the cartridge or pre-filled syringe in the guard has been used to deliver its medication, the shield is moved distally until it reaches the guarded position. In the guarded position, the stop tabs on the body abut the proximal edges of the windows, preventing further distal movement. As the shield is moved, the detents on the shield leave the proximal detent pockets, preferably because of sloping edges on the proximal detent pockets, and slide along the body until they enter a set of distal detent pockets when the shield reaches the guarded position. The distal detent pockets may have blunt or oblique proximal edges, which prevent the shield from being returned proximally, and thereby substantially lock the shield in the guarded position for disposal. Preferably, the proximal edges of the detent pockets are inclined at an angle corresponding substantially to the proximal edges of the detents to maximize bearing surface engagement therebetween.

In a first preferred embodiment, the guard has only two parts, namely a body and a shield, which are pre-assembled in the unguarded position ready to receive a cartridge. In this embodiment, the body includes a finger grip integrally molded onto its proximal end, preferably defining a "T" shape, having locking detents formed on the finger grip. A cartridge, preferably and typically a conventional unit dose pre-filled syringe including a needle and needle cover on its distal end and a plunger and flange on its proximal end, is inserted into the proximal end of the body until it is fully encapsulated within the cavity. Once fully inserted, the proximal end of the pre-filled syringe engages the locking detents on the finger grip, substantially permanently locking the pre-filled syringe into the guard. Once locked into the guard, the needle and its cover on the pre-filled syringe extend at least partially through the distal openings in the body and shield and preferably beyond their distal ends.

After medication is dispensed, the shield is slid into the guarded position, using one or two hands, preferably only requiring one hand. During use, the index and middle fingers are generally placed on the finger grip adjacent the shield, while the thumb directs the plunger on the pre-filled syringe. To move the shield, the free hand may be used to slide the shield, or the thumb and ring finger of the same hand may be moved to the finger grip to hold the body. The index and middle fingers may hold the sides of the shield and move it distally, thereby sliding the shield until it is locked in the guarded position.

In a second preferred embodiment, the guard includes an attachable finger grip plug and a plunger, in addition to the body and shield. The plunger, with or without a thumb ring, a button plunger, or a "T" handle on one end, is attachable to the piston of a conventional unit dose cartridge. The finger grip plug may include a finger grip thereon, such as a pair of wings or an octagonal flange. The finger grip plug and the proximal end of the body include cooperating members for locking the finger grip section to the body and preventing the cartridge within the body from moving substantially axially. Preferably, the finger grip plug has locking detents thereon, and the proximal end of the body includes an annular-shaped collar having tapered pockets therein adapted to receive the locking detents.

The body and shield are generally provided pre-assembled in the unguarded position, as previously described, with the finger grip plug and plunger furnished separately. A cartridge, preferably a unit dose glass cartridge having a needle and needle cover on its distal end and a piston in its proximal end, is inserted into the proximal end of the body until it is fully encapsulated within the cavity. Once fully inserted, the finger grip plug is attached to the body, by aligning the locking detents on the finger grip section with the tapered pockets in the collar. The locking detents are inserted into the pockets until they engage, substantially permanently and/or releasably enclosing the cavity and encapsulating the cartridge therein. In addition, the detents on the finger grip plug may substantially add engage the proximal end of the cartridge, thereby preventing the needle on the cartridge from withdrawing proximally into the body during use.

In addition, the plunger may include a radially extending detent or tab that is compressed when the plunger is directed into the finger grip plug. The tab resiliently returns to its extended position once the plunger is fully inserted into the finger grip plug, thereby preventing the plunger from being removed therefrom.

Once the guard, cartridge and finger grip plug are assembled, the needle and needle cap on the cartridge extend through the distal ends of the shield and body. The plunger is attached to the piston in the cartridge, such as by a threaded bore on the distal end of the plunger which is adapted to screw into a threaded nipple on the piston. The device is then ready to be used to deliver medication to a patient. After medication is dispensed, the shield is slid into the guarded position, as with the first embodiment, with one or two hands.

In additional preferred embodiments, the syringe guard includes a body and a sliding shield similar to that described above, for holding a unit dose pre-filled syringe having its own plunger. In particular, the guard includes a mechanism on the proximal end of the body, preferably on or within the finger grip, for substantially permanently (or releasably under certain conditions) securing the syringe within the guard and substantially preventing distal and/or proximal movement of the syringe received therein. More preferably, the locking mechanism requires the syringe to be inserted into the guard in a predetermined orientation, thereby facilitating viewing of a label or the like on the cartridge through the windows in the guard.

For example, the mechanism may include a clip or ring for clasping the finger grip and the proximal flange of the syringe together. Preferably, a pair of clips are provided which slide over and engage the distal and proximal surfaces respectively of the finger grip and the flange of the syringe.

Alternatively, the body may include an annular member within the open end thereof for creating an interference fit with the barrel of the syringe inserted into the guard. Preferably, an annular ring extends radiantly into the cavity, thereby frictionally engaging an enlarged proximal end of the syringe directed into the cavity to prevent removal of the syringe.

In a further alternative, the finger grip has a substantially rectangular shape including a recess in the proximal end for receiving the flange or the proximal end of the pre-filled syringe. One or more tabs or detents extend into the recess from one or more walls of the finger grip for engaging the flange of the syringe to secure it within the guard.

Alternatively, the finger grip may include a latch or cover for enclosing the recess once a syringe is inserted therein, the latch preferably being attached to the finger grip by a hinge along a wall defining the recess. Once the flange of the syringe is directed into the recess, the latch is closed, preferably engaging a tab within the recess to prevent the latch from coming loose and releasing the syringe. The latch also preferably includes an aperture for accommodating a plunger of the syringe received within the body.

In a final preferred embodiment, the syringe guard is adapted to receive relatively small cartridges or pre-filled syringes, for example a 0.5 mL unit dose pre-filled syringe including a rigid nose shield or needle cap having a diameter larger than the barrel of the syringe. The guard includes a body having a mechanism in its proximal end for lockably engaging the proximal end of the pre-filled syringe received therein, such as those described above. In addition, the body includes one or more semi-rigid members, for example pairs of tabs or longitudinal ribs, extending along the cavity for engaging the barrel of the syringe. The body may also include one or more lead-in ribs at or near the proximal end of the cavity for guiding the pre-filled syringe during insertion. When the syringe is inserted into the body, the cap engages the tabs as it enters the cavity. The tabs are forced radially out to allow the cap to pass through the cavity. Once the cap extends beyond the proximal end of the body, the tabs resiliently return to abut or engage the wall of the barrel, thereby preventing substantial lateral movement of the syringe within the body during use. The tabs also preferably prevent the rails of the guard body from being compressed after use to prevent inadvertent release of the cooperating locking detents on the shield and body.

As will be understood, the present invention provides an improved guard for medical cartridges or pre-filled syringes that may include as few as two parts, but generally has no more than four parts. The device may be used for a wide variety of conventional prepackaged medications or drugs, such as anesthesia, anti-thrombotic drugs, biological drugs or vaccines, for use within the medical and/or dental fields, where the cartridge or pre-filled syringe is generally disposed of after a single use. Because the device is relatively simple, the parts may be provided in standard configurations. For example, a single shield design may be provided that fits on a variety of bodies for receiving cartridges or pre-filled syringes made by different manufacturers. In addition, the distal openings in the body and/or the shield may be provided in a plurality of sizes to accommodate a variety of needle caps, luer adapters and the like. Thus, the guard may be more easily mass produced, reducing manufacturing costs, and thereby providing a more competitively priced disposable syringe guard.

In addition, the rectangular configuration of the present device provides improved rigidity, thereby affording greater protection to the cartridge held in the guard. Although the cartridge or pre-filled syringe is fully encapsulated within the guard, the windows in the guard allow the medical or dental professional to effectively monitor the cartridge or pre-filled syringe and the medication being delivered.

Finally, the slidable shield and cooperating detents allow the user to operate the guard using only one hand, thereby allowing their other hand to be free to perform other necessary tasks, such as restraining a young patient or providing improved access to the target region for the needle. Once the shield is locked in the guarded position, the device may be disposed of safely if used properly, substantially eliminating concerns that the needle may become exposed and cause an accidental stick.

Accordingly, it is a principal object of the present invention to provide an improved unit dose syringe device that is easy to manufacture and convenient to use.

It is also an object to provide an improved syringe guard that affords improved protection for a cartridge or pre-filled syringe encapsulated therein but still allows effective monitoring of the medication being dispensed.

Other objects and features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which:

FIGS. 5A and 5B are perspective views of the syringe guard holding a pre-filled syringe, with the shield in an unguarded position, and ready to be used to deliver medication to a patient.

FIGS. 8A, 8B, 8C and 8D are perspective views of the body of the syringe guard of FIG. 7.

FIGS. 9A and 9B are perspective views of the shield of the syringe guard of FIG. 7.

FIG. 16A is a perspective view of a fifth preferred embodiment of a syringe guard holding a pre-filled syringe, with the shield in the guarded position.

FIG. 16B is a detail of the syringe guard of FIG. 16A, showing the detents retaining the syringe in the syringe guard.

FIG. 16C is a detail of an alternate embodiment of the detents shown in FIG. 16B.

FIG. 16D is a detail of another alternate embodiment of the detents shown in FIG. 16B.

FIG. 17C is a cross-section of the syringe guard of FIG. 17A taken along line C—C.

FIG. 17D is a cross-section of the syringe guard of FIG. 17B taken along line D—D.

FIG. 17E is an end view of the syringe guard of FIG. 17A.

FIG. 21A is a side view of an alternative embodiment of the syringe guard body of FIG. 8A for receiving relatively short unit dose ampules.

FIG. 21B is a perspective view of the syringe guard body of FIG. 21A, holding a short unit dose cartridge therein.

FIG. 21C is a detail of the syringe guard of FIG. 21A.

DETAILED DESCRIPTION OF THE PREFERRED EMBODIMENTS

Figure 1:
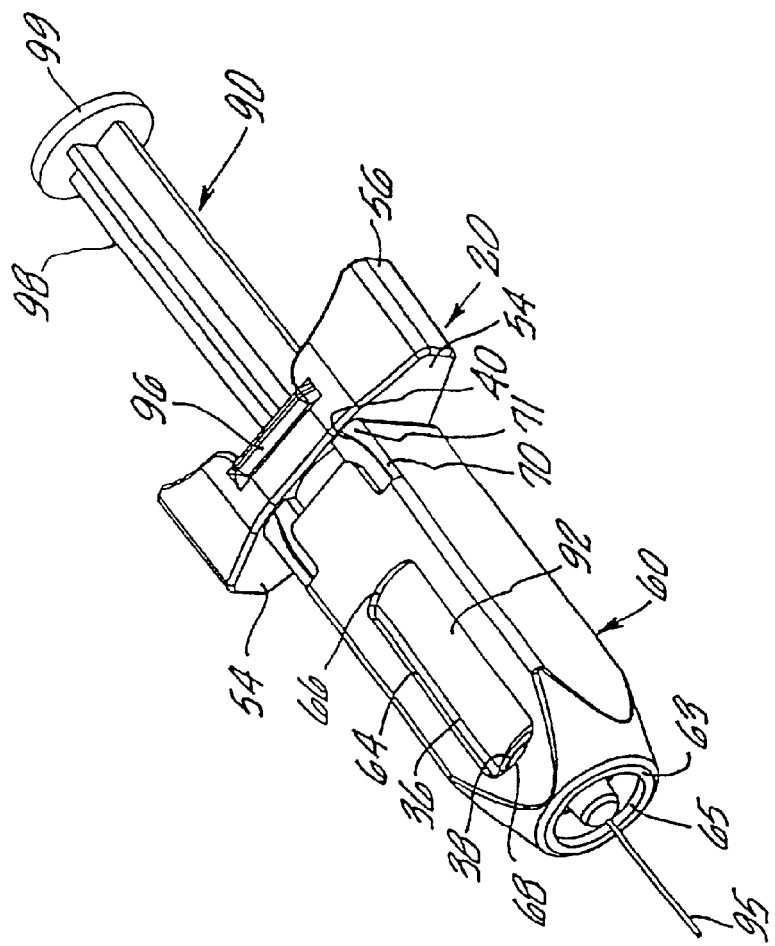
FIG. 1 is a perspective view of a first preferred embodiment of the syringe guard of the present invention, holding a pre-filled syringe.

Turning to the drawings, FIG. 1 shows a first preferred embodiment of the present invention, namely a syringe guard 10 for holding a pre-filled unit dose syringe 90. Generally, the guard 10 comprises two parts, namely a housing or body 20 for receiving and holding the pre-filled syringe 90, and a protective case or shield 60 slidably attached to the body 20. Both the body 20 and the shield 60 are generally molded from plastic, such as polypropylene, K-Resin® (a synthetic resinous polymer of butadiene and styrene), or polycarbonate, and are preferably clear and substantially colorless to facilitate observation of the pre-filled syringe received therein. Alternatively they may be translucent or opaque, and may be colored, such as a latex color, or a flesh tone, such as off-white, brown, or black.

Figure 2A:
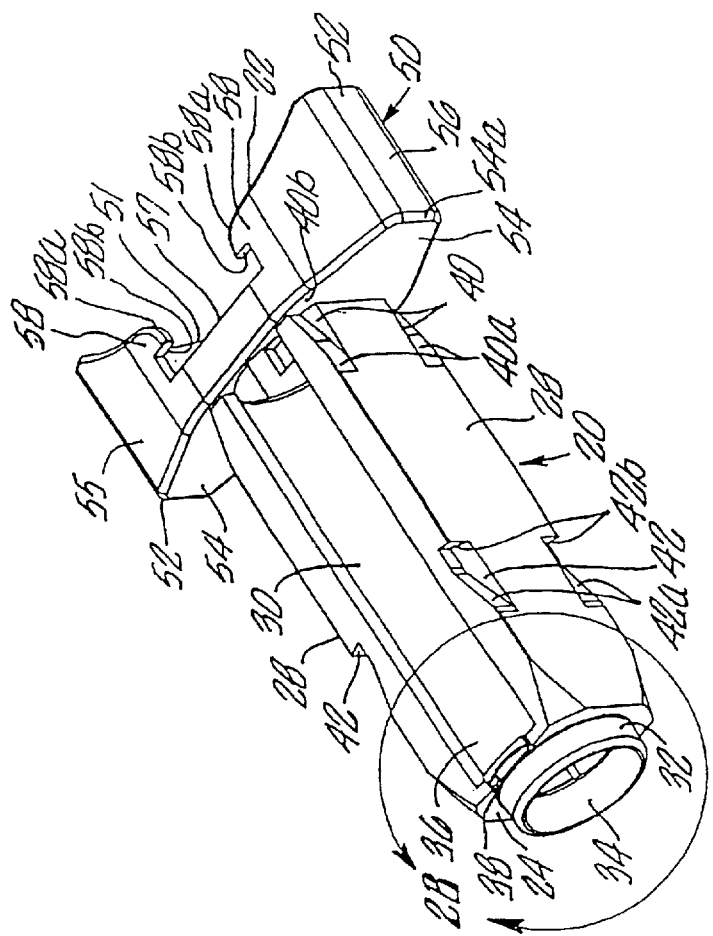
FIGS. 2A, 2B and 2C are perspective views of the body of the syringe guard of FIG. 1.
Figure 2B:
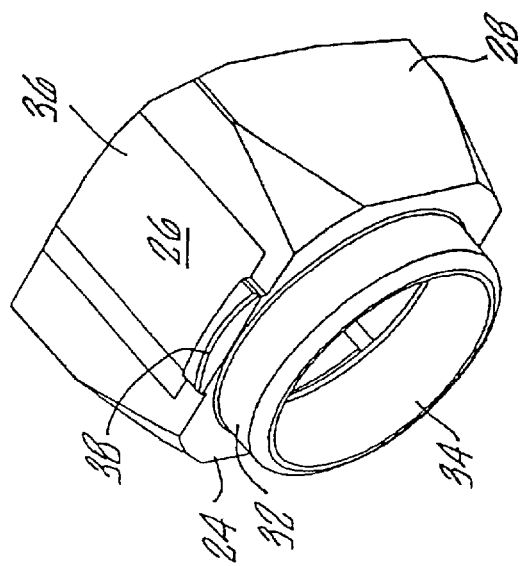
Figure 2C:
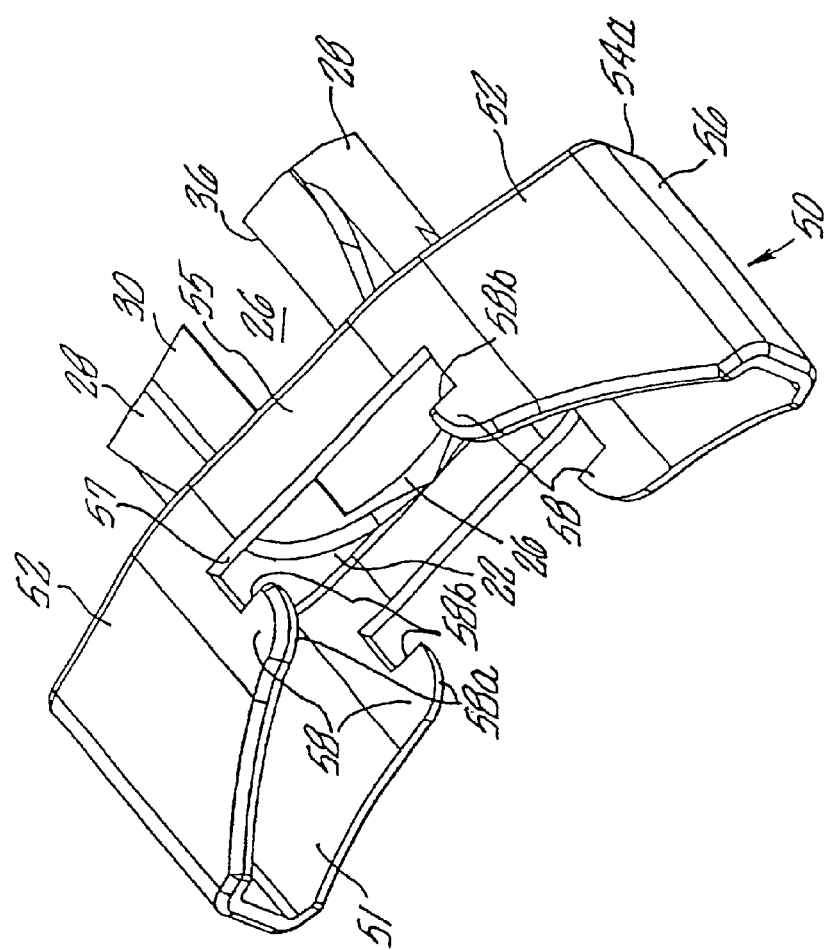

Turning to FIGS. 2A, 2B and 2C, the body 20 is an elongate member, preferably having a substantially rectangular cross-section, comprising two side rails 28, an open proximal end 22, and an open distal end 24. The rectangular shape is preferred as it provides superior rigidity, protecting the syringe therein from lateral forces that might otherwise damage it, particularly if the syringe is made of glass. Alternatively instead of the rectangular cross-section, the body and shield may have corresponding oval or round cross-sections providing sufficient rigidity to protect the cartridge received therein.

In addition, the body 20 has a substantially rigid collar 32 on the distal end 24, and a finger grip 50 on the proximal end 22, both attached to or preferably integrally molded onto the body 20. Alternatively, instead of comprising side rails 28, the body 20 may comprise a substantially rectangular body having four side walls (not shown).

The two side rails 28 generally have a "C" shape and define a cavity 26 in the body 20, the cavity 26 extending axially from the proximal end 22 to the distal end 24 of the body 20. The inside surface 30 of the rails 28 is preferably concave, conforming substantially to the outer diameter of a standard unit dose pre-filled syringe. Alternatively, if the side rails 28 have a flat or "C" channel inside surface 30, guide rails (not shown) or the like may be provided on the inside surface 30 to direct the pre-filled syringe 90 (FIG. 4) into the cavity 26 and hold it, thereby substantially preventing lateral movement which may damage the pre-filled syringe 90.

As shown in FIGS. 2A and 2C, the finger grip 50 generally comprises a pair of wing-like members 52 molded onto the proximal end 22 of the body 20, thereby generally defining a "T" shape. Each wing-like member 52 includes a distal surface or finger ledge 54, and an outer gripping surface 56 extending proximally from the outer edge 54a of the finger ledge 54. The outer gripping surface 56 may include a lip, grooves or other irregularities (not shown) protruding radially from its proximal end or set in the surface 56, if desired to improve the hold on the finger grip 50. Lateral surfaces 55 extend proximally from the finger ledges 54 between the gripping surfaces 56, thereby defining a recess or open proximal end 51 communicating with the cavity 26 in the body 20. The lateral surfaces 55 of the finger grip 50 include a plurality of locking detents 58 partially defining an aperture or slot 57 for holding the pre-filled syringe (not shown in FIGS. 2A and 2B) inserted into the cavity 26, as will be described further below.

Turning to FIG. 2B, the collar 32 extending from the distal end 24 preferably has a substantially annular shape, including an opening 34 extending therethrough adapted to allow the needle and needle cover on the pre-filled syringe (not shown) in the cavity 26 to extend beyond the body 20. The opening 34 preferably has a diameter smaller than the cavity 26, such that the distal end 24 substantially retains the pre-filled syringe inside the cavity 26, preventing distal movement. Alternatively, the distal end 24 may be tapered or otherwise partially obstructed, as long as it engages the distal end of the pre-filled syringe, preventing distal movement of the pre-filled syringe, and does not substantially interfere with the needle and cover extending beyond the distal end 24.

The distal end 24 may include an expandable "collet" (not shown) defined by a plurality of longitudinal slots extending proximally a short distance from the distal end 24. The collet may have a diameter smaller than that of the syringe barrel, hub or needle cap as desired, thereby allowing the distal end 24 to be resiliently expanded to substantially engage the syringe received therein. In a further alternative, the opening 34 in the distal end 24 may have a sufficiently large diameter to freely allow the distal end of the pre-filled syringe to extend therethrough, the pre-filled syringe being locked substantially within the body exclusively by a locking mechanism on the proximal end 22 or finger grip 50 of the body 20, as described more particularly below, and not by a collar on the distal end 24.

The side rails 28 define two elongate openings or windows 36 extending longitudinally between the finger grip 50 and the distal end 24, allowing observation of the pre-filled syringe held in the body 20. Alternatively, if a four-walled body is provided, an elongate opening or window may be integrally formed in one or more of the side walls, preferably in two walls on opposite sides of the body 20. The body 20 also includes one or more stop tabs 38 attached or molded directly to the body 20. Preferably, stop tabs 38 are molded onto the body 20 on two opposite sides of the distal end 24 of the body 20.

The body 20 also includes one or more sets of detent pockets, preferably having a set of proximal detent pockets 40 adjacent the finger grip 50, and a set of distal detent pockets 42 at a more distal location on the body 20. The detent pockets lock the relative movement between the shield 60 and body 20, as is explained more fully below.

Figure 3A:
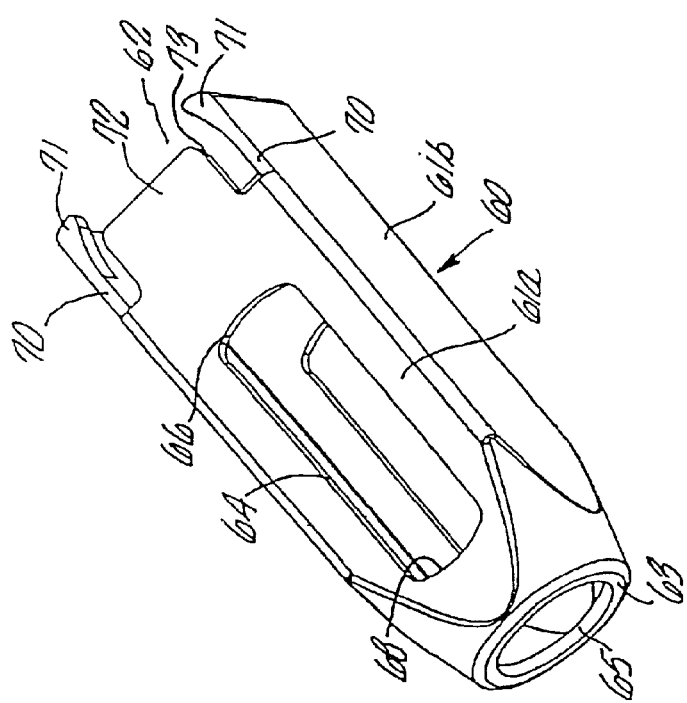
FIGS. 3A and 3B are perspective views of the shield of the syringe guard of FIG. 1.
Figure 3B:
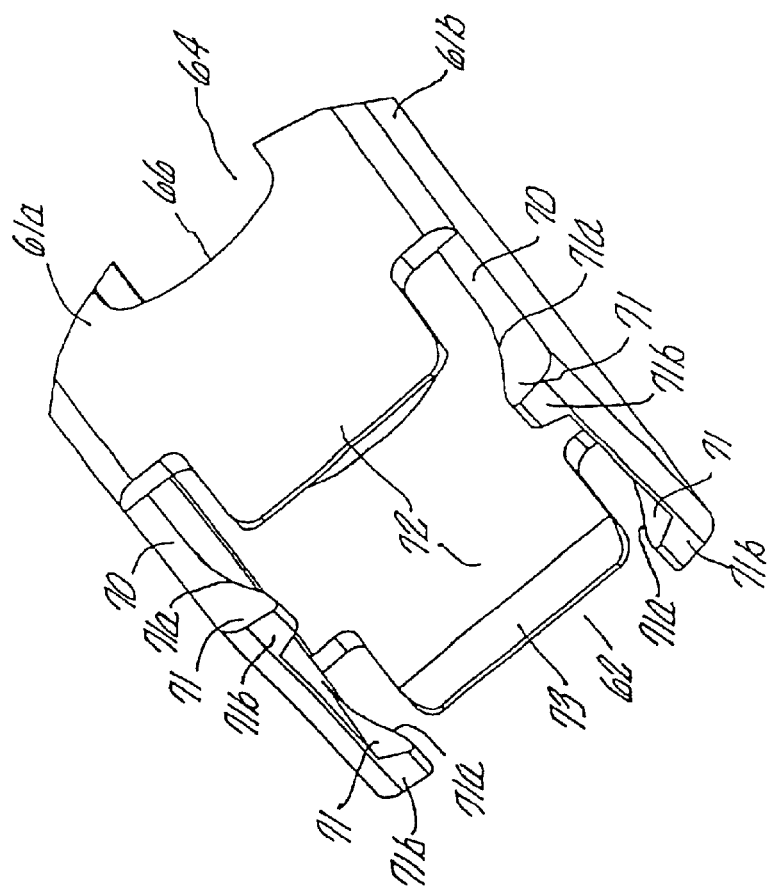

Turning now to FIGS. 3A and 3B, the protective case or shield 60 is a tubular member adapted to slidably fit on the body 20, preferably having a substantially rectangular interior shape which conforms to the shape of the body 20. The shield 60 includes four side walls 61a, 61b, an open proximal end 62, and an open distal end 63. The shield 60 has a pair of detent arms 70 and a plurality of detents 71 attached to or preferably integrally molded directly into the side walls 61b. Assembly tabs 72 with sloping or ramped interior surfaces 73 are molded into and extend proximally from the side walls 61a.

The detents 71 preferably have shapes corresponding substantially to the shapes of the detent pockets 40, 42 in the body 20. The proximal edges 71b are blunt or preferably oblique to engage the proximal surfaces 40b or 42b as described below and to maximize bearing surface area, particularly to stabilize a shorter guard 10. In addition, the detent arms 70 may include indents 170 for controlling the flexural strength of the detent arms 70 as the arms 70 vary in size and thickness in embodiments adapted to accommodate a variety of syringes.

At least one wall 61a, preferably the two opposite walls 61a, includes an elongate opening or window 64 therethrough. The window 64 allows observation of the pre-filled syringe received in the body 20, and also provides a traveling slot for the stop tab 38 on the body 20. The window 64 has a proximal edge 66 and a distal edge 68 defined by the wall 61a which limit the relative movement of the shield 60 to the body 20, as will be explained more fully below. Alternatively, the window 64 may be divided by a cross-member (not shown), molded into the wall 61a which extends transversely across the window 64 if it is desired to further limit the movement of the shield 60.

Optionally, the sidewalls 61a, 61b may include wings, a ring or similar finger holds (not shown) extending radially from the shield 60 to ease movement of the shield 60 in relation to the body 20. In addition, the side walls 61a, 61b may provide a flat surface onto which a label may be applied, for example to identify the drug or other fluid contained within the pre-filled syringe 90 received within the guard 10, or an embossed pattern may be molded, possibly including a name or a logo.

Figure 4:
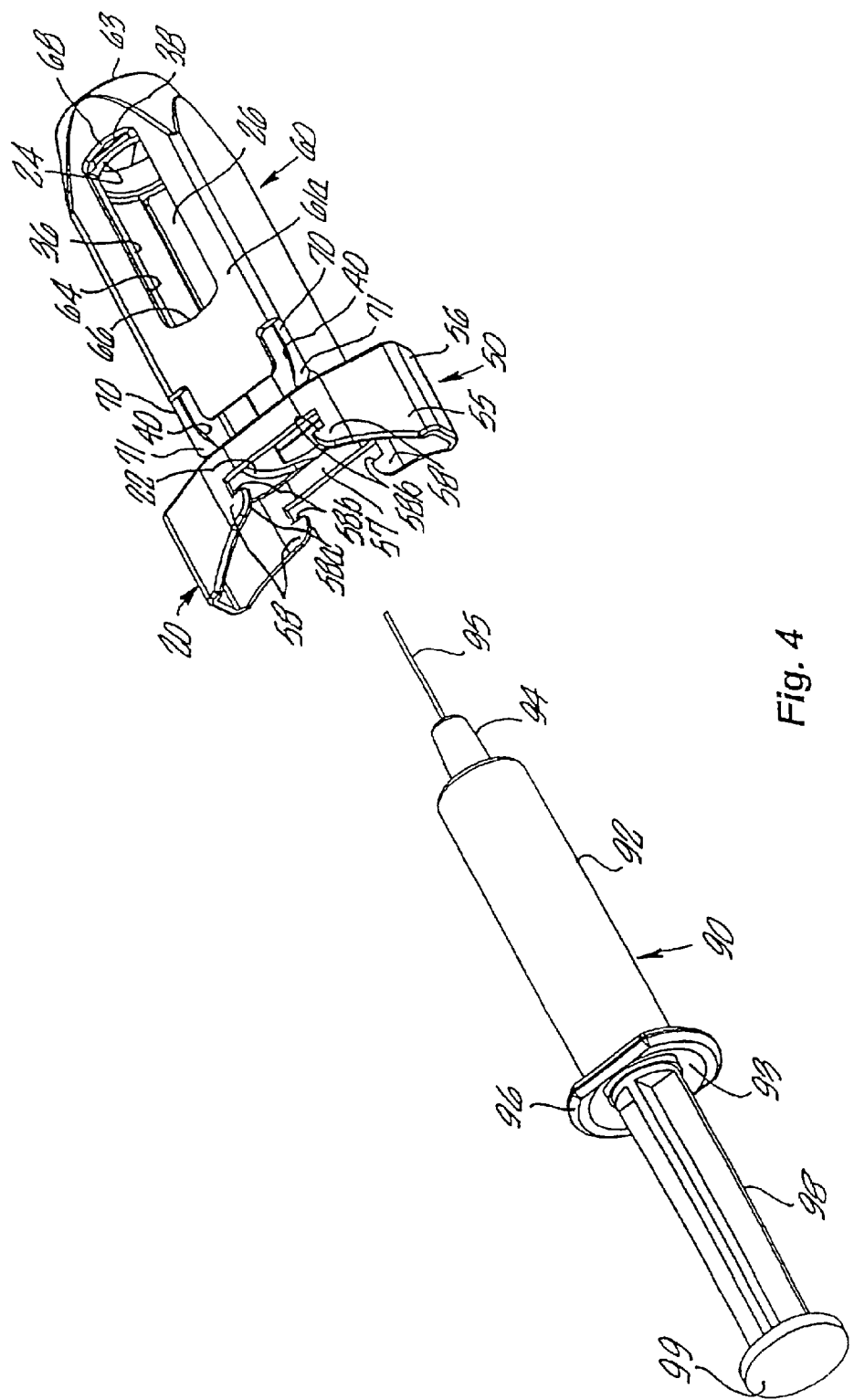
FIG. 4 is a perspective view of the pre-assembled syringe guard about to receive a conventional pre-filled syringe therein.

Turning to FIG. 4, the guard 10 is normally provided with the body 20 and shield 60 pre-assembled as shown. To assemble the guard 10, the distal end 24 of the body 20 (see FIG. 2A) is inserted into the open proximal end 62 (see FIG. 3A) of the shield 60, with the window 36 in the body 20 aligned with the side wall 61a of the shield 60 having the window 64 therein. As the body 20 is inserted, the stop tab 38 (the stop tab and window not shown on the opposite side operate substantially the same way) engages the tapered interior edge 73 of the assembly tab 72 on the shield 60 (see FIG. 3B), allowing the stop tab 38 to pass under the wall 61a. After the stop tab 38 passes under the wall 61a, it then enters the window 64 where it may freely travel.

Figure 6A:
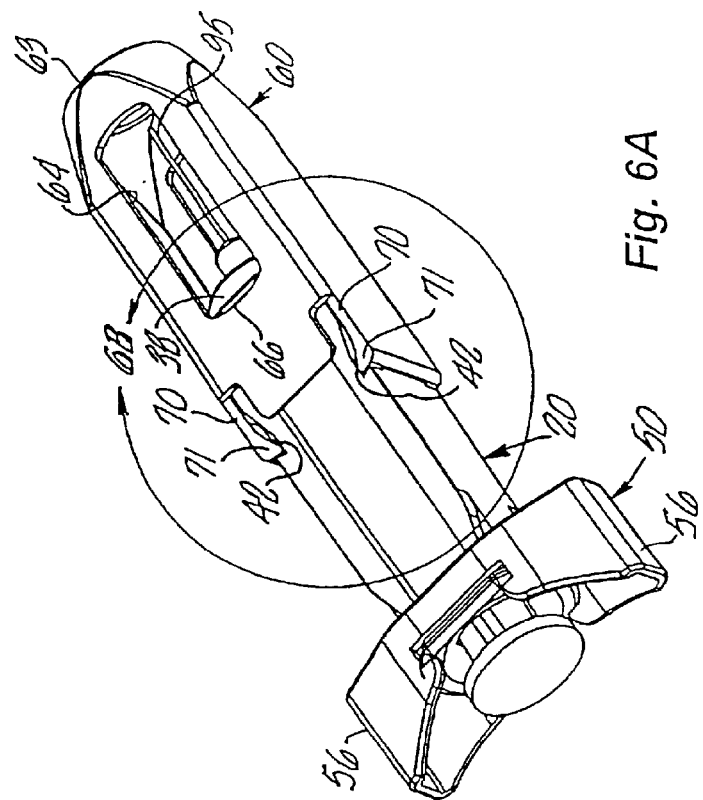
FIGS. 6A and 6B are perspective views of the syringe guard holding a pre-filled syringe, with the shield locked in a guarded position after medication has been dispensed from the syringe.
Figure 6B:
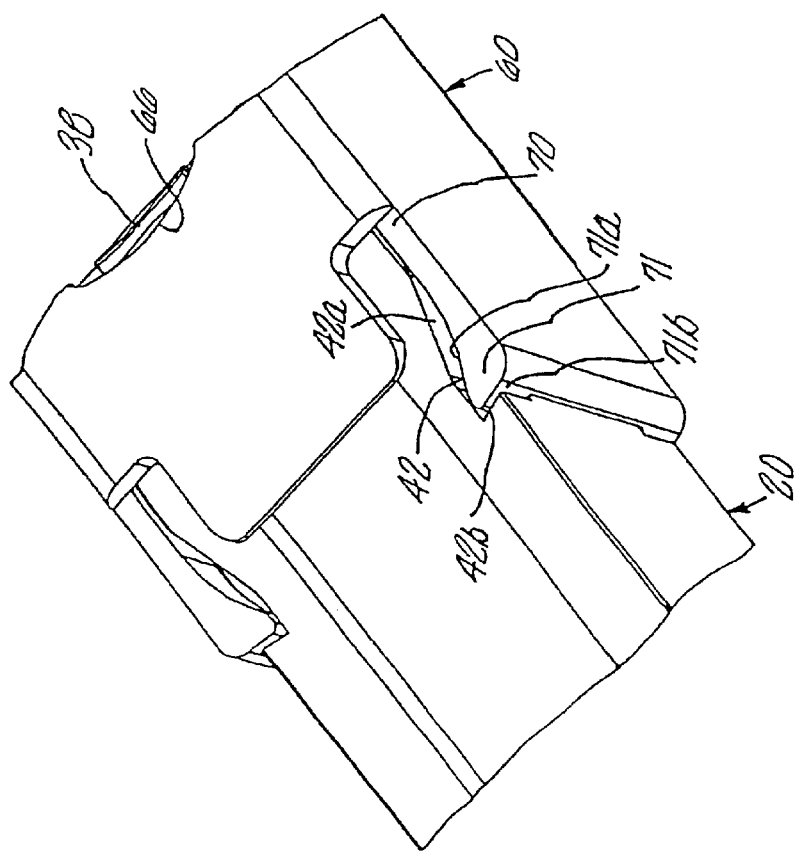

Together, the stop tab 38 and window 64 allow the shield 60 to slidably move in relation to the body 20, but substantially define the limits of that relative movement. The shield 60 may slide proximally and distally until the stop tab 38 abuts a distal edge 68 and a proximal edge 66, respectively, of the window 64. Specifically, when the stop tab 38 engages the distal edge 68 of the window 64, as shown in FIG. 4, the shield 60 is in a proximal or unguarded position. When the stop tab 38 engages the proximal edge 66 of the window 64, as shown in FIGS. 6A and 6B, the shield is in a distal or guarded position.

Referring to FIGS. 5A and 5B, when the stop tab 38 abuts the distal edge 68 of the window 64, the cooperating detents 71 and proximal detent pockets 40 operate to hold the shield 60 in the unguarded position. The sloping distal edges 71a of the detents 71 engage the sloping distal edges 40a of the proximal detent pockets 40 on the body 20, thereby preventing the shield 60 from moving distally.

Turning again to FIG. 4, once assembled, the guard 10 is ready to receive a cartridge, such as a conventional unit dose pre-filled syringe 90. Although the pre-filled syringe 90 shown in FIGS. 1 and 4 is the preferred delivery system for use with the syringe guard of the present invention, it will be appreciated that the syringe guard may be used for other pre-filled or unit dose delivery systems, and that the term cartridge includes other such known systems. The pre-filled syringe 90 generally has a substantially smooth-walled cylindrical barrel 92, a distal end or hub 94 including a hypodermic needle 95, a needle cover or cap (not shown), an enlarged proximal end 93 having a flange 96, and a plunger 98. The flange 96 generally includes a flat edge 96a in a predetermined orientation with a label or graduation marks 92a on the barrel 92 of the pre-filled syringe 90. Preferably, the flange 96 includes two opposite flat edges 96a extending between two curved edges 96b, thereby defining a generally rectangular-shaped finger grip 96. The flange 96 may have a sufficiently large width to provide a finger grip for the pre-filled syringe 90, or may simply be a small lip to facilitate manufacturing, for example on a filling line.

The distal end 94 of the pre-filled syringe 90 is inserted into the recess 51 of the finger grip 50 and the open proximal end 22 of the body 20. The pre-filled syringe 90 enters the cavity 26 and progresses distally until the distal end 94 of the pre-filled syringe 90 becomes coextensive with and/or directly engages the distal end 24 of the body 20. The distal end 94 of the pre-filled syringe 90 may simply abut the distal end 24 of the body 20, or alternatively the distal end 94 may partially enter the opening 34 and engage the collar 32, thereby providing additional protection from lateral movement of the pre-filled syringe 90 (FIGS. 1 and 6A).

As the pre-filled syringe 90 becomes fully encapsulated within the cavity 26, the flange 96 on the proximal end 93 of the pre-filled syringe 90 contacts the locking detents 58 on the finger grip 50. The locking detents 58 have tapered proximal edges 58a, allowing the pre-filled syringe 90 to be directed further distally, the flange 96 moving the locking detents 58 aside and entering the slot 57. As is shown in FIGS. 5A and 5B, the locking detents have blunt distal edges 58b which prevent the syringe 90 from being removed proximally from the slot 57, thereby substantially permanently locking the pre-filled syringe 90 into the body 20, an important feature of the present invention. Thus, the slots 57 preferably substantially permanently lock the proximal end 93 of the pre-filled syringe 90 within the finger grip 50, thereby preventing axial (i.e. proximal and/or distal) movement of the syringe 90 within the guard 10.

Although the pre-filled syringe 90 is considered substantially permanently encapsulated within the guard 10, the material of the finger grip 50 may have sufficient flexibility to allow a tool (not shown) to move the detents 58 to allow the pre-filled syringe 90 to be removed from the body 20. Preferably, the tool applies a distal force to each of the proximal edges 56a of the outer surface 56, causing the lateral surfaces 55 and detents 58 to expand outward to release the flange 96. Alternatively, the tool may engage the lateral surfaces 55 directly and force them outward to release the flange 96 from the slots 57.

Thus, if an incorrect pre-filled syringe 90 is inserted into the guard 10 during factory assembly, it may be released from the guard 10 without damaging the guard 10 and/or the pre-filled syringe 90, thereby allowing both to be reused. This may be particularly important for pre-filled glass syringes for which the flange 96 is often structurally the weakest point of the pre-filled syringe 90. Thus, a pre-filled glass syringe 90 may be releasably encapsulated within the guard 10, allowing removal of the syringe 90 under certain controlled conditions. The finger grip 50, however, is sufficiently rigid that, during normal use for example by a medical professional, the pre-filled syringe 90 will not be removable from the guard 10.

In addition, the generally rectangular-shaped flange 96 may establish a preferred orientation for the pre-filled syringe 90 to be received in the guard 10. Preferably, the shape of the flange 96 allows the pre-filled syringe 90 to be received within the slots 57 only in an orientation that allows the label 92a to be visible through the window 64 of the guard 10 during use (see FIG. 5A). For example, the detents 58 may engage the opposing flat edges 96a of the flange 96 (not shown), thereby preventing the pre-filled syringe 90 from being rotated axially within the body 26. Alternatively, the finger grip 50 the body 20 may be provided with any symmetrical or predetermined shape adapted to correspond substantially to the shape of the flange 96 on a cartridge or pre-filled syringe 90 being received therein, thereby encapsulating the cartridge within the body in a predetermined orientation about the longitudinal axis of the cartridge. For example, an elliptical or oval finger grip (not shown) may provide an appropriate alternative shape, or a round finger grip (not shown) may be provided if it has a recess having a shape corresponding to that of the flange 96 on the pre-filled syringe 90.

Referring to FIGS. 1 and 5A, once the pre-filled syringe 90 is locked into the guard 10, the needle 95 and its cover (not shown) extend through the opening 34 on the collar 32 and the opening 65 on the distal end 63 of the shield 60. The distal end 63 of the shield 60 has a generally tapered configuration defining an opening 65 through which the needle 95 may extend. Preferably, the length of the shield 60 is substantially coextensive with the barrel 92 of the pre-filled syringe 90, allowing the full length of the needle 95 to extend beyond the distal end 63 of the shield 60, but protecting the hub 94 of the pre-filled syringe 90.

The opening 65 is generally circular and has a diameter larger than that of the syringe barrel 92 and/or hub 94, and may be provided with a variety of diameters or configurations to facilitate use of the pre-filled syringe 90. For example, the diameter of the opening 65 may be sufficiently large to allow a luer adapter (not shown) or other alternative distal tip to be provided on the pre-filled syringe 90 or to be attached to the hub 94 during use. Most preferably, however, the opening 65 has a diameter sufficiently small to minimize the risk of accidental sticks, for example to prevent a finger from being directed into the shield 60 after use.

The pre-filled syringe 90 encapsulated within the guard 10 may then be used in a conventional manner to deliver the medication in the barrel 92. The medical professional typically holds the pre-filled syringe by placing his or her index finger on a finger ledge 54, his or her middle finger on the other finger ledge 54, and his or her thumb on the end 99 of the plunger 98. The cover (not shown) is removed, the needle 95 is inserted into the patient, and the medication is delivered by directing the plunger 98 distally with the thumb. As can be seen from FIGS. 1 and 5A, the windows 64 and 36 provide constant observation of the barrel 92 of the pre-filled syringe 90, allowing the user to closely monitor delivery of the medication. The finger grip 50 also preferably has a sufficiently large size relative to the flange 96 to provide improved manipulation by the user as compared to using the pre-filled syringe 90 alone.

After the medication is dispensed, the needle 95 is withdrawn from the patient, and the self-shielding feature of the guard 10 is engaged. The user holds the body 20, typically by placing his ring finger on the gripping surface 56 adjacent his middle finger, and moving his thumb from the plunger 98 to the other gripping surface 56. The index and middle fingers, already adjacent the side walls 61b of the shield 60, grip the walls 61b and are moved distally, thereby sliding the shield 60 distally until it reaches the guarded position, shown in FIG. 6A. Alternatively, while one hand holds the finger grip 50, the shield 60 may be directed to the guarded position with the free hand of the user.

Because the cooperating detents 71 and detent pockets 40 hold the shield 60 in the unguarded position, force must be applied to move the shield 60 distally. As previously discussed, the detents 71 have sloping distal edges 71a and blunt or oblique proximal edges 71b (FIG. 3B), and similarly, the proximal detent pockets 40 have sloping distal edges 40a and blunt or oblique proximal edges 40b (FIG. 5B). Because of the sloping distal edges 71a, 40a, the engagement between the detents 70 and the proximal detent pockets 40 may be overcome by pushing the shield 60 distally in relation to the body 20. The detent arms 70 move radially outward as the detents 71 move distally up the sloping edges 40a until the detents 71 leave the detent pockets 40. The shield may then be moved freely, the stop tab 38 traveling along the window 64, until the stop tab 38 abuts the proximal edge 66 of the window 64, reaching the guarded position.

As shown in FIG. 6A, because of the predetermined location of the distal detent pockets 42, when the stop tab 38 reaches the proximal edge 66 of the window 64, the detents 71 substantially simultaneously enter the distal detent pockets 42. The blunt or oblique proximal edges 71b of the detents engage the similarly shaped proximal edges 42b of the distal detent pockets 42, thereby preventing the shield 60 from being moved proximally. The corresponding shape of the engaged proximal edges 71b, 42b may also maximize bearing surface to prevent misalignment of the shield 60. Furthermore, because the stop tab 38 abuts the proximal edge 66 of the window 64, the shield 60 may not be moved further distally. Thus, the shield 60 is thereby substantially permanently locked in the guarded position.

As can be seen from FIG. 6A, when the shield 60 is moved distally into the guarded position, the distal end 63 of the shield 60 passes over the needle 95, covering the needle 95. Once the shield 60 is locked in the guarded position, the needle 95 is no longer accessible, thereby substantially eliminating the risk of accidental sticks, and preventing reuse of the syringe 90. The guard 10 and pre-filled syringe 90 may then be disposed of safely.

Figure 10:
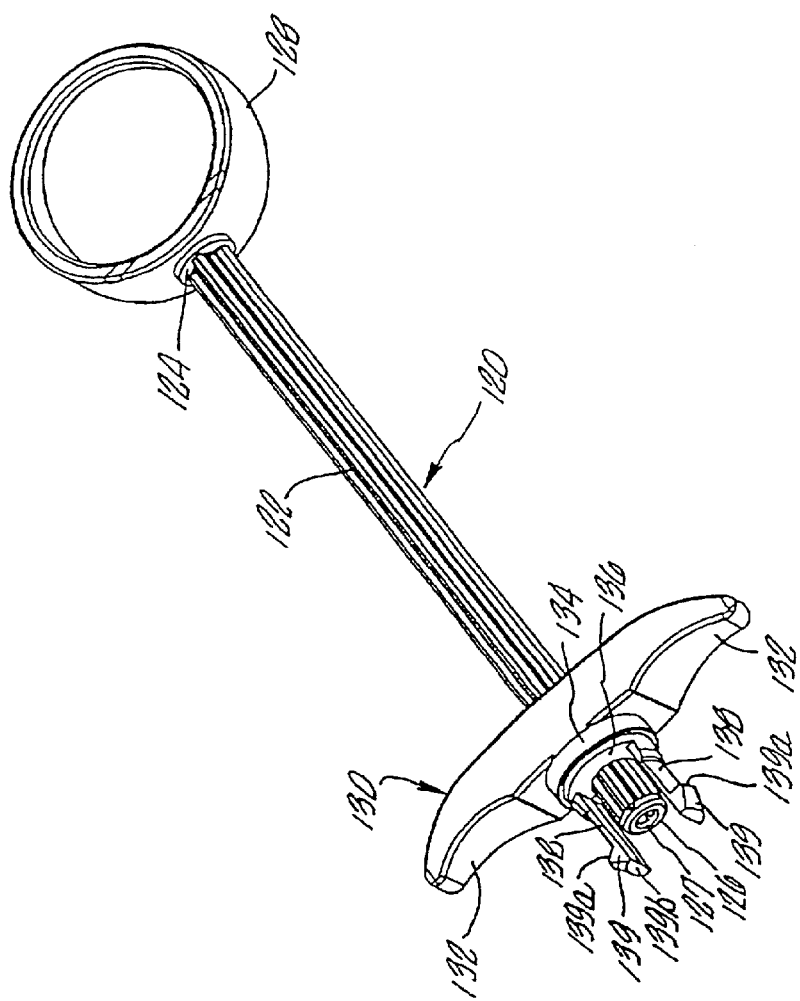
FIG. 10 is a perspective view of the finger grip plug and plunger of the syringe guard of FIG. 7.
Figure 11:
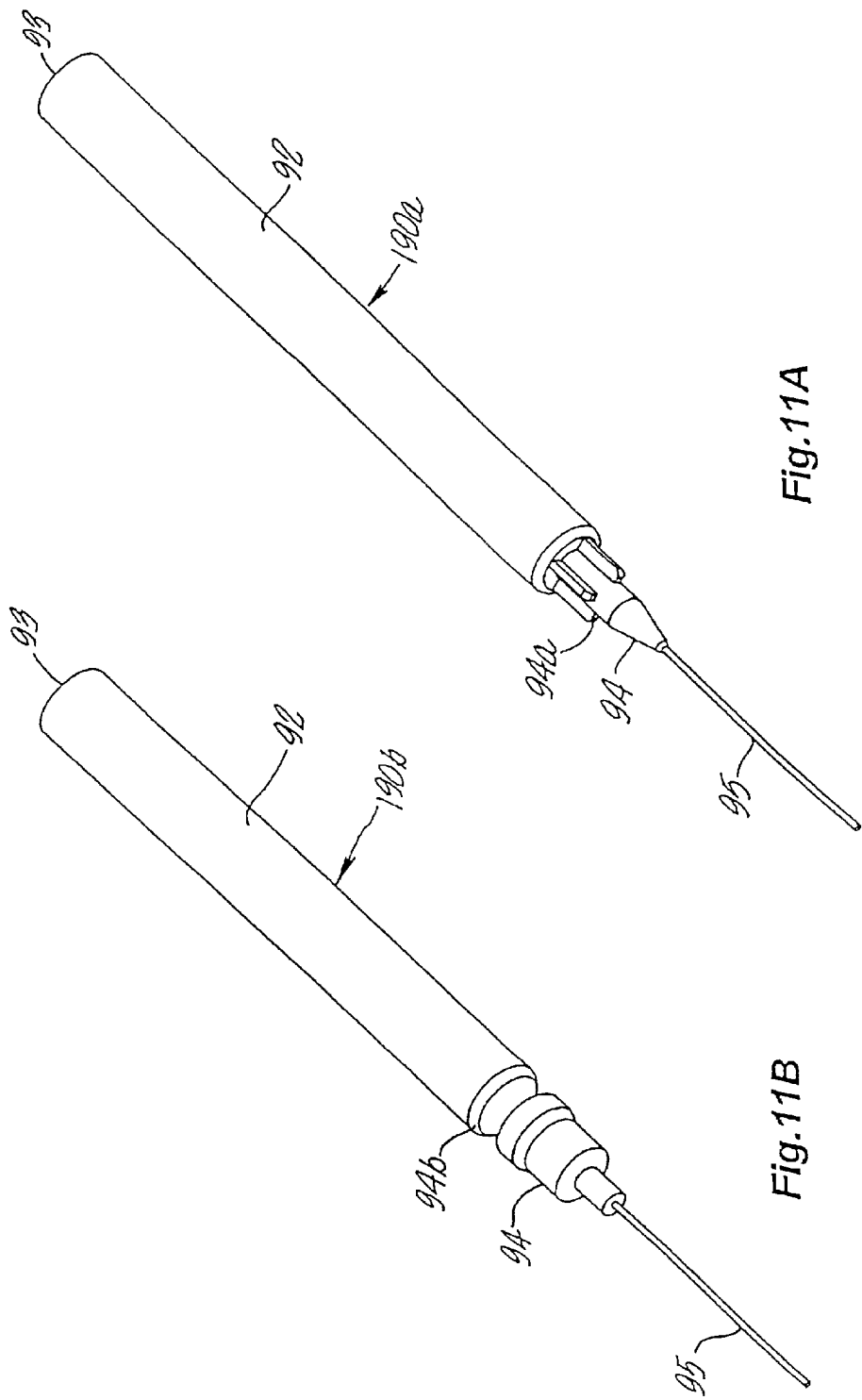
FIGS. 11A and 11B are perspective views of standard unit dose cartridges.

Turning now to FIGS. 7–13, and 22–23, a second preferred embodiment is shown, namely a syringe guard 10 for holding a unit dose cartridge manufactured without its own plunger, such as the unit dose glass cartridges 190 made by Carpuject and Tubex (see FIGS. 11A and 11B). Generally, the guard 10 comprises four parts, namely a housing or body 20 for receiving and holding the cartridge 190, a protective case or shield 60 slidably attached to the body 20, a finger grip plug 130, and a plunger 120. As before, the parts are molded from plastic, such as polypropylene, K-Resin® (a synthetic resinous polymer of butadiene and styrene), or polycarbonate, having a clear, colorless finish.

Figure 8C:
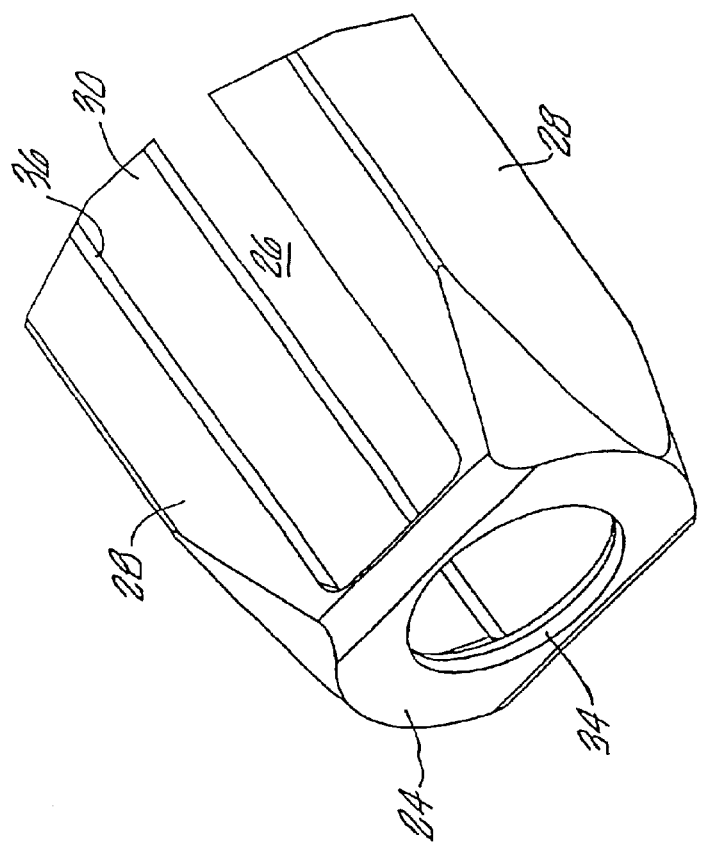

Turning to FIG. 8A, the body 20 has two elongate side rails 28, a proximal end 22 and a distal end 24. As shown in FIG. 8B, a collar 32 is molded directly on the distal end 24 and has an opening 34 therethrough. Alternatively, as in FIG. 8C, it may be appropriate to provide the distal end 24 with the opening 34 formed directly through it and eliminate the collar 32.

The two side rails 28 have concave inside surfaces 30 conforming substantially to the outer diameter of a standard unit dose cartridge (not shown in FIG. 8A), thereby defining a cavity 26 in the body 20 for holding the cartridge. The outer edges of the side rails 28 define a substantially rectangular cross-section for the body 20, providing a substantially rigid structure for protecting the cartridge encapsulated within the body 20. In addition, the side rails 28 define two elongate openings or windows 36 extending between the proximal end 22 and the distal end 24, thereby allowing observation of the cartridge. The body 20 also includes one or more stop tabs 38 molded onto the body 20, preferably on two opposite sides of the distal end 24. Similar to the previous embodiment, the body 20 also includes a set of proximal detent pockets 40 adjacent the finger grip collar 110 (or ring 112), and a set of distal detent pockets 42 at a more distal location on the body 20.

Figure 8D:
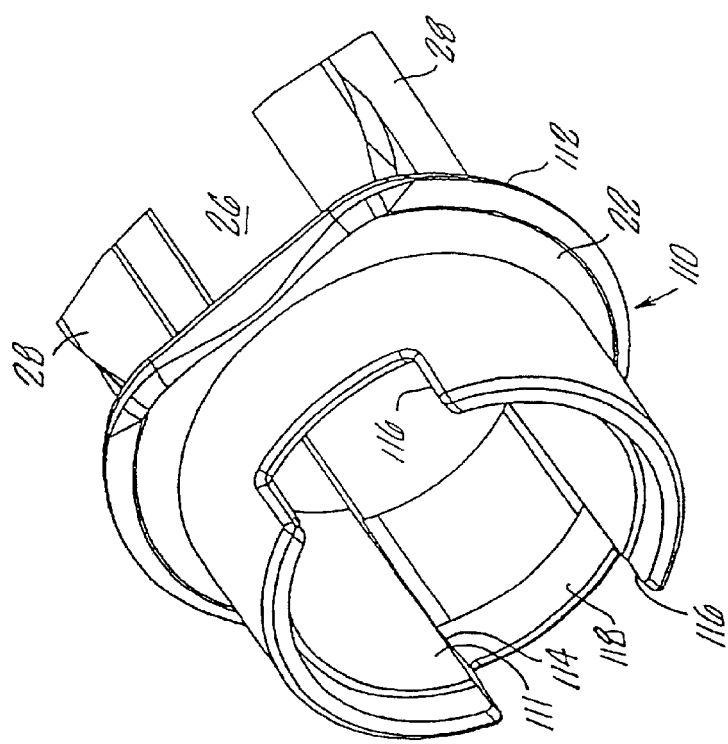

Turning to FIG. 8D, the proximal end 22 of the body 20 includes a finger grip collar 110, preferably molded directly thereon. The finger grip collar 110 has a circular opening 111 extending through it, communicating with the cavity 26 in the body 20. Tapered grooves 114 are formed on the inside the finger grip collar 110, defining tapered pockets 118 used to attach the finger grip plug 130 to the body 20. Notches 116 are formed in the finger grip collar 110 adjacent the tapered grooves 114 to provide easy orientation during attachment. The finger grip collar 110 also includes a finger grip ring 112 which extends radially out from the distal end of the finger grip collar 110, allowing the body 20 to be held more easily.

Turning now to FIGS. 9A and 9B, the protective case or shield 60 is a tubular member adapted to slidably fit on the body 20, similar to the shield previously described. The shield 60 includes four side walls 61a, 61b, an open proximal end 62, and an open distal end 63. The shield 60 has a pair of detent arms 70 and detents 71 molded into the side walls 61b. Assembly tabs 72 with tapered interior surfaces 73 are molded into and extend proximally from side walls 61a. Finger holds 76 are molded onto and extend radially from the side walls 61a.

The two opposite walls 61a each include elongate windows 64a, 64b which allow observation of the cartridge in the body 20. The distal window 64a also provides a traveling slot for the stop tab 38 on the body 20. Each window 64a has a proximal edge 66 defined by a cross-member 164 and a distal edge 68 defined by the wall 61a. The windows 64a and the stop tabs 38 together limit the relative movement of the body 20 and the shield 60, as previously described.

Figure 22:
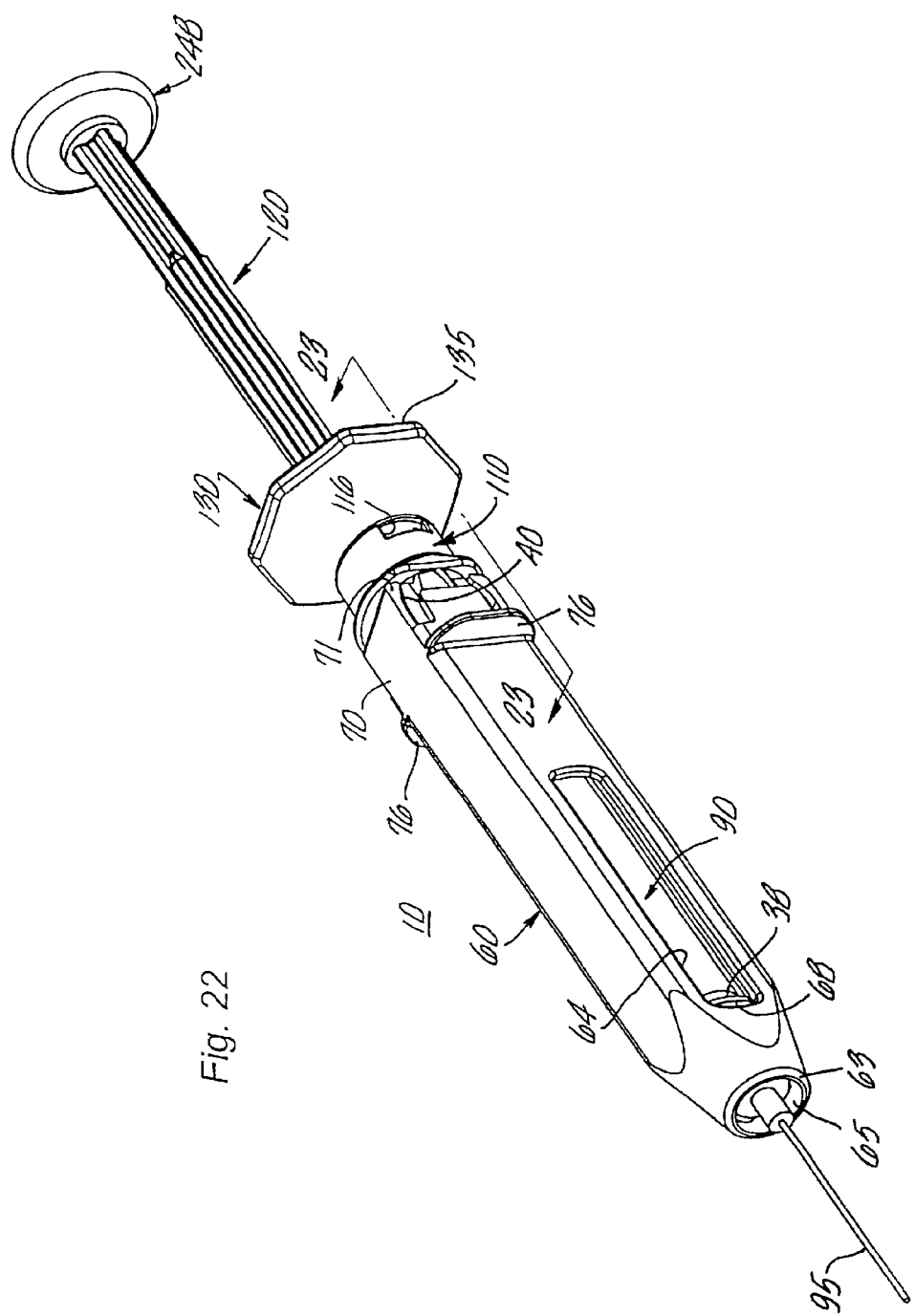
FIG. 22 is a perspective view of an alternative embodiment of the syringe guard of FIG. 7.
Figure 23:
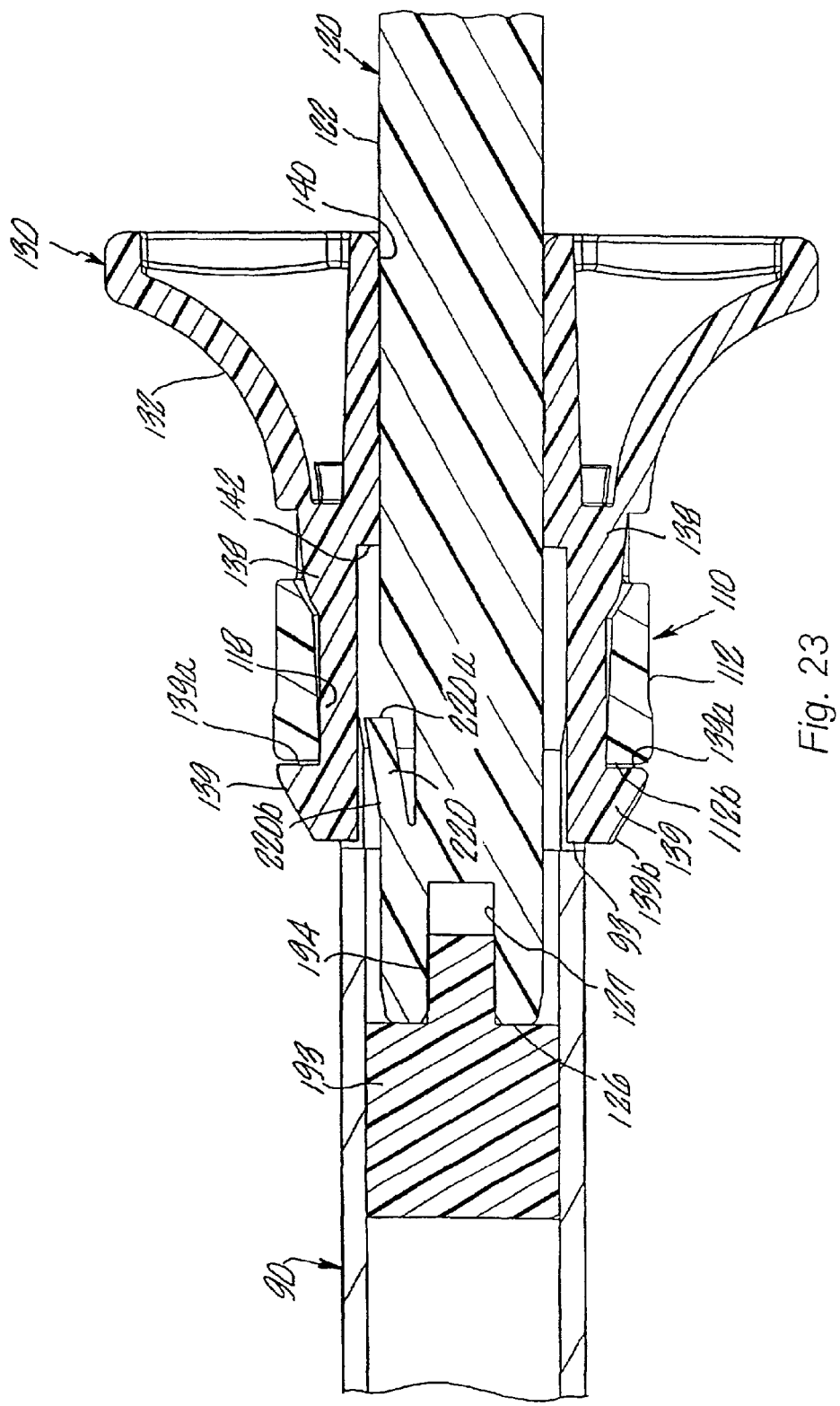
FIG. 23 is a cross-sectional detail of the syringe guard of FIG. 22, taken along line 23—23.

Referring now to FIGS. 10, 22, and 23, the plunger 122, preferably having a cruciform cross-section, has a thumb ring 128 on its proximal end 124 (FIG. 10), and a threaded bore 127 on its distal end 126. The threaded bore 127 is a shallow hole having a standard thread pattern, adapted to screw onto the threaded nipple 194 on the piston 193 on a conventional medical cartridge 190 (FIG. 23). Alternative distal ends 126 may be provided, such as a harpoon, a threaded nipple, an adhesive material, molded ribs, a frictional surface or the like (not shown), if appropriate for attaching to the piston of a desired medical cartridge. In addition, alternative proximal ends may be provided, such as a button end 248 (FIG. 22), or a "T" type thumb grip (not shown), instead of the thumb ring 128.

In addition, the plunger 120 may also include a one-way locking member that allows the plunger 120 to be substantially permanently inserted into the finger grip plug 130. Preferably, as shown in FIG. 23, the locking member includes a semi-rigid tongue or tab 220 formed adjacent the distal end 126 of the plunger shaft 122. The tab 220 extends proximally and radially out from the plunger shaft 122, but may be compressed against the shaft 122 to facilitate insertion distally into the finger grip plug 130. Once inserted, the tab 220 resiliently returns to its extended position to prevent withdrawal of the plunger 130 from the finger grip section 130, as described more particularly below.

Returning to FIG. 10, the finger grip plug 130 comprises a central hub 134, a pair of finger ledges 132 extending radially from the hub 134, and a pair of fingers or legs 138 extending distally from the hub 134. Alternatively, instead of the pair of finger ledges or wings 131, the finger grip plug 130 may include a substantially symmetrical grip, such as an octagonal finger grip 135 as are often used on dental syringes (FIG. 22). The hub 134 also has a passage extending axially through it, adapted to receive the plunger 120. The fingers 138 include locking detents 139, which are described more fully below.

Figure 12:
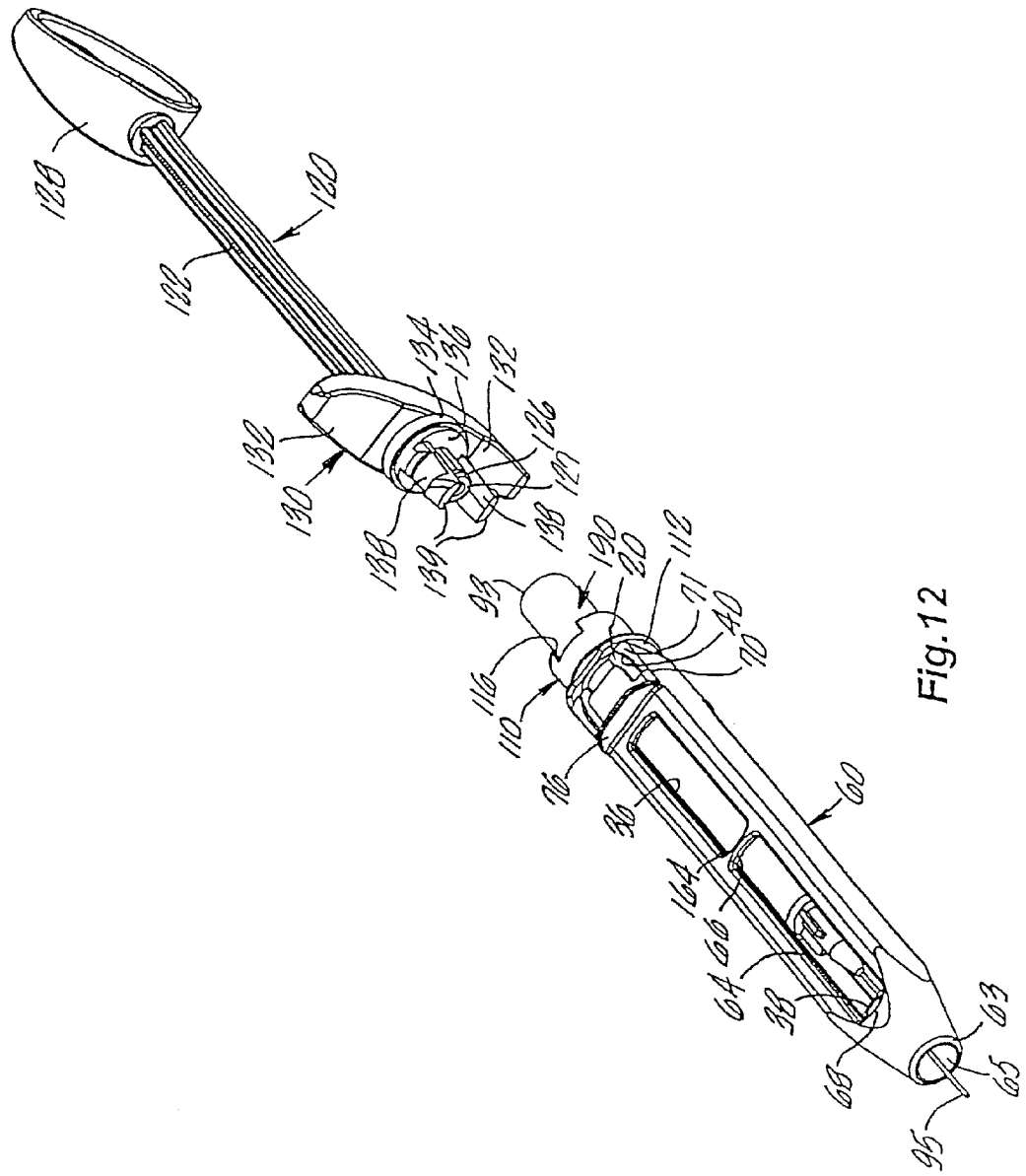
FIG. 12 is a perspective view of the syringe guard with a unit dose cartridge partially inserted into the body, and with the plunger assembly aligned and ready to be attached to the body.

Turning to FIG. 12, the guard 10 is normally provided with the body 20 and shield 60. pre-assembled and the plunger 120 and finger grip plug 130 loose. To pre-assemble the body 20 and shield 60, the distal end 24 of the body 20 (see FIG. 8A) is inserted into the proximal end 62 of the shield 60 (see FIG. 9A), with the window 36 in the body 20 aligned with the wall 61a of the shield 60 having the windows 64a, 64b therein. The stop tab 38 includes a sloped or ramped distal edge 38a that engages the tapered interior edge 73 of the assembly tab 72 (see FIG. 9B), allowing the stop tab 38 to pass under the wall 61a until it enters the proximal window 64b. The ramped distal edge 38a also allows the stop tab 38 to pass under the cross-member 136, until it enters and travels freely in the distal window 64a. The detent arms 70 are directed radially outward to prevent them from engaging the distal detent pockets 42, and then the shield 60 is directed proximally until the detents 71 engage the proximal detent pockets 40, holding the shield 60 in the unguarded position.

The pre-assembled body 20 and shield 60 are then ready to receive a cartridge, such as the conventional unit dose glass cartridges 190a and 190b shown in FIGS. 11A and 11B respectively, although alternatively, the device may be used to hold other vials, or ampules. The cartridges 190 generally comprise a barrel 92, a distal end or hub 34 including a hypodermic needle 95, a needle cover or cap (not-shown), and a proximal end 93 having a threaded piston therein 193 (see FIG. 23).

Turning again to FIG. 12, the distal end 94 of the cartridge 190 is inserted into the open proximal end 22 of the body 20. The cartridge 190 enters the cavity 26 and progresses distally until the distal end 94 of the cartridge 190 extends through or engages the distal end 24 of the body 20. Because different types of distal ends are provided on different cartridges, the distal point of engagement between the body 20 and the cartridge 190 may vary. For example, a standard Carpuject cartridge 190a, shown in FIG. 11A, requires the body 20 to have a distal end 24 similar to that shown in FIG. 8C, such that the distal ribs 94a on the cartridge 190a enter the opening 34 in the distal end 24 of the body 20. In contrast, a standard Tubex cartridge 190b, shown in FIG. 11B, requires a distal end 24 on the body 20 such as the collar 32 shown in FIG. 8B, thereby allowing the edge 94b on the cartridge 190b to engage the collar 32.

Figure 13:
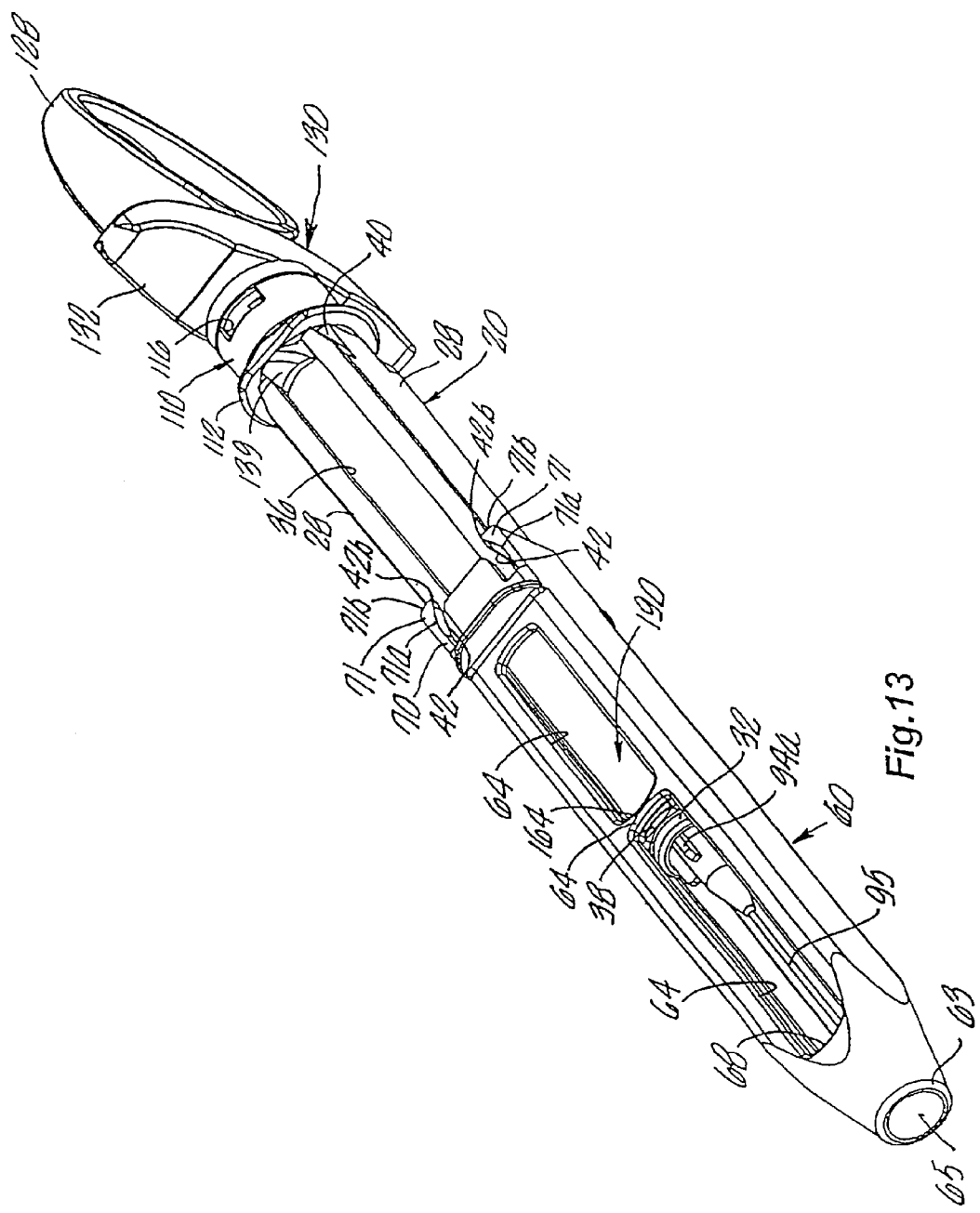
FIG. 13 is a perspective view of the syringe guard holding a cartridge, with the shield locked in the guarded position after medication has been dispensed from the cartridge.

Turning to FIGS. 12 and 13, once the cartridge 190 is fully inserted into the cavity 26, the finger grip plug 130 is attached to the body 20. The fingers 138 on the finger grip plug 130 are aligned with the notches 116 in the finger grip collar 110 on the body 20. The fingers 138 are inserted into the notches 116, compressing the fingers radially as they enter the tapered pockets 118 (FIG. 8D) and pass through the collar 110. Upon reaching the windows 36, the fingers 138 expand radially outward again. The locking detents 139 have blunt proximal edges 139a which engage the distal side 112b of the finger ring 112, thereby substantially permanently locking the finger grip plug 130 to the body 20.

Preferably, when the finger grip plug 130 is locked onto the body 20, the cartridge 190 is simultaneously encapsulated within the cavity 26 (FIG. 23). The body 20 generally has a length corresponding substantially to that of the cartridge 190. When the finger grip plug 130 is locked onto the body 20, the distal ends 139b of the fingers 138 then preferably engage the proximal end 93 of the cartridge 190, substantially preventing proximal movement of the cartridge 190.

In addition, the body 20 may be used to encapsulate a cartridge 190 that is substantially shorter than the length of the body 20 but has a similar diameter to that of the cavity 26. As shown in FIGS. 21A–21C, the distal end 24 may include one or more tabs 240 formed thereon for securing a cartridge, such as the standard Tubex cartridge 190b (see FIG. 11B), within the body 20. Preferably, a pair of semi-rigid tabs 240 are provided on the distal end 24 of the body 20 extending partially into the opening 34, each tab 240 having a generally ramped inner surface 240a and a substantially blunt distal surface 240b. The inner surface 240a preferably defines a diameter smaller than that of the hub 94 of the cartridge 190, while the diameter of the opening 34 is smaller than that of the barrel 92.

The tabs 240 are ramped distally inward, thereby allowing the hub 94 to be directed distally past the tabs 240, forcing the tabs 240 slightly outward. Once the hub 94 extends beyond the tabs 240, the tabs 240 resiliently snap back inward, the blunt distal edge 240b engaging the blunt proximal edge 94a of the hub 94. Thus, the opening 34 substantially prevents distal movement of the cartridge 190, while the tabs 240 prevent proximal movement.

Alternatively, the cavity 26 may include one or more tabs, annular ridges or similar retaining detents (not shown) at predetermined locations in the body 20 corresponding to the length of one or more short cartridges. When the cartridge 190 is directed into the body 20, the smooth-walled barrel 92 passes freely over the tab or ridge, preferably facilitated by a ramped proximal edge thereof. When the cartridge 190 is fully inserted into the body 20, the needle 95 should extend beyond the distal end 24 and the proximal end 93 should be engaged by a blunt distal edge of the tab or ridge, thereby preventing the cartridge 190 from withdrawing proximally into body 20 during use.

As shown in FIGS. 12, 13 and 23, with the cartridge 190 fully inserted into the body 20, the plunger 120 is then attached to the piston 193 in the cartridge 190, preferably by screwing the threaded bore 127 on the plunger 122 to a threaded nipple 194 on the piston 193. As described above, the plunger shaft 122 preferably includes a tab 220 for substantially permanently retaining the distal end 126 of the plunger 120 within the finger grip plug 130. The finger grip plug 130 includes a passage 140 extending distally therethrough for receiving the plunger 120. The passage 140 includes a lip 142, preferably extending radially about the passage 140, for engaging the tab 220 to substantially retain the plunger 120.

The tab 220 includes a ramped distal surface 220b which allows it to be forced inward when the distal end 126 of the plunger 120 is directed into the passage 140. Once the tab 220 passes distally beyond the lip 142, it resiliently returns to its outward extended position. If the plunger 120 is drawn proximally, the blunt proximal edge 220a abuts the lip 142, thereby preventing the plunger 120 from being pulled out of the finger grip plug 130. In addition, the plunger shaft 122 may have a cross-section similar in size to the passage, preventing the fingers 138 from being forced radially inward and thereby further securing the finger grip plug 130 to the body 20 of the syringe guard 10.

Figure 7:
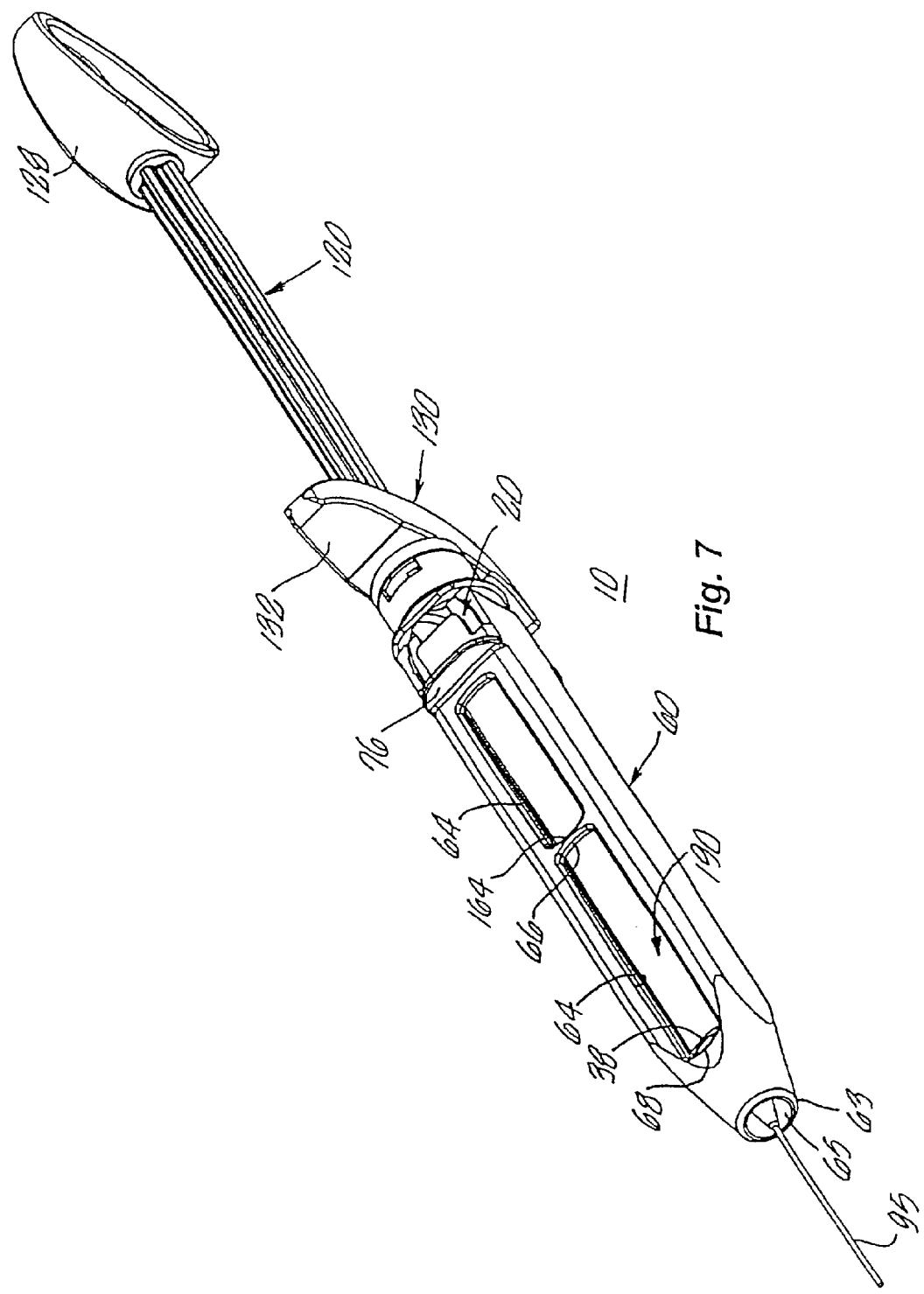
FIG. 7 is a perspective view of another preferred embodiment of the syringe guard holding a unit dose cartridge, with the shield in the unguarded position, and ready to be used to deliver medication to a patient.

Referring to FIG. 7, with the shield 60 in the unguarded position, the needle 95 of the cartridge 190 extends through the opening 65 and beyond the distal end 63 of the shield 60. The device is then ready to be used to deliver the medication contained within the cartridge 190. Similar to the procedure described above, the user places his index and middle fingers on the finger ledges 132, and his thumb in the ring 128. The needle cover (not shown) is removed, the needle 95 is inserted into the patient, and the medication is dispensed by directing the plunger 122 distally with the thumb. As shown in FIG. 7, the windows 64 and 36 allow constant observation of the barrel 92 of the cartridge 190, allowing the user to closely monitor delivery of the medication.

After the medication is dispensed, the needle 95 is withdrawn from the patient, and the self-shielding feature of the guard 10 is engaged, similar to the procedure described previously. As the shield 60 is moved distally, the detents 70 leave the proximal detent pockets 40. When the shield reaches the guarded position, the detents 71 enter the distal detent pockets 42, locking the shield 60.

Figure 14C:
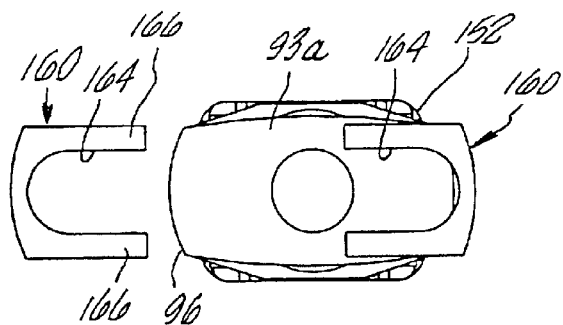
FIG. 14C is a top view of the syringe guard of FIG. 14A.
Figure 14A:
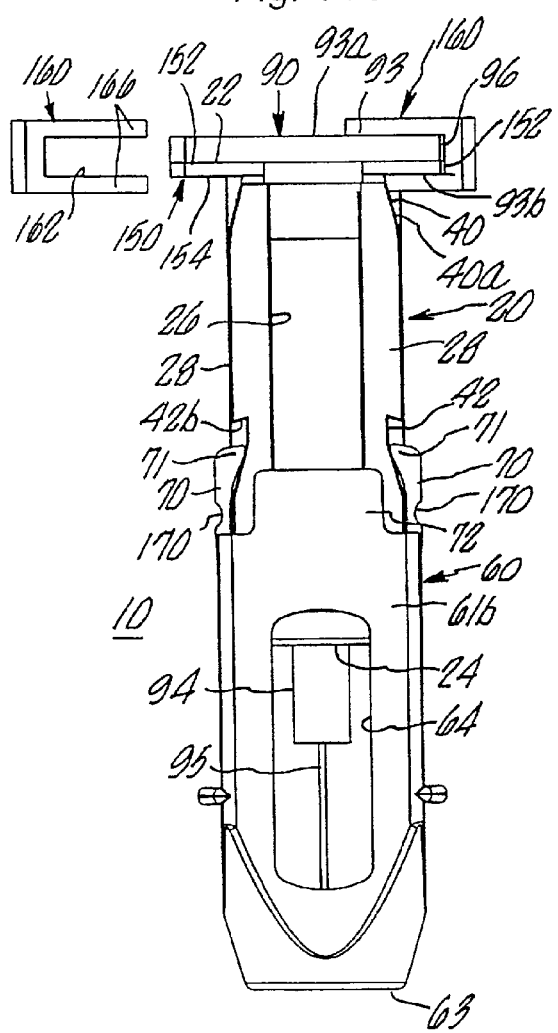
FIG. 14A is a side view of a third preferred embodiment of a syringe guard holding a pre-filled syringe, with the shield in the guarded position.
Figure 14B:
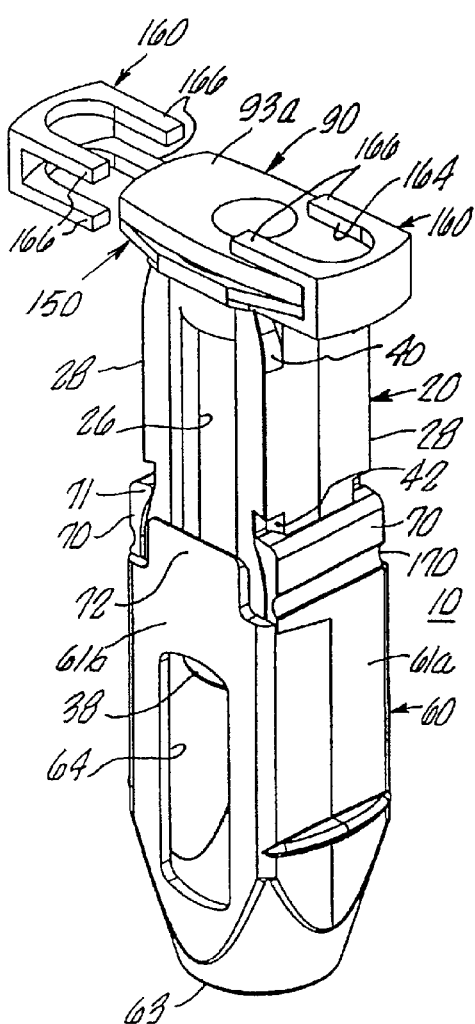
FIG. 14B is a perspective view of the syringe guard of FIG. 14A.
Figure 15C:
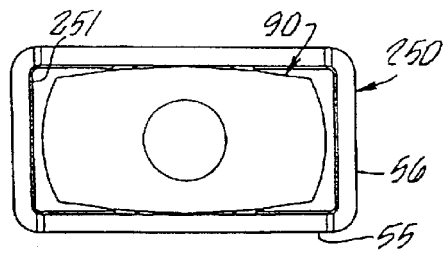
FIG. 15C is a top view of the syringe guard of FIG. 15A.
Figure 15D:
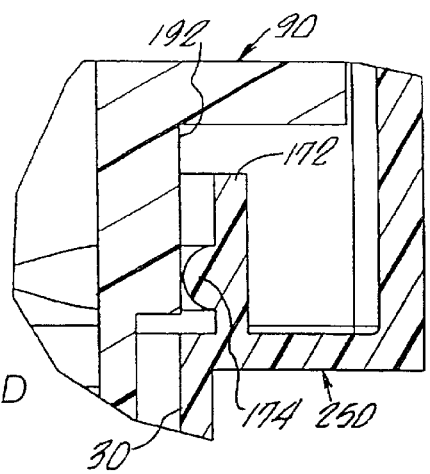
FIG. 15D is a detail of the cross-section of FIG. 15B.
Figure 15B:
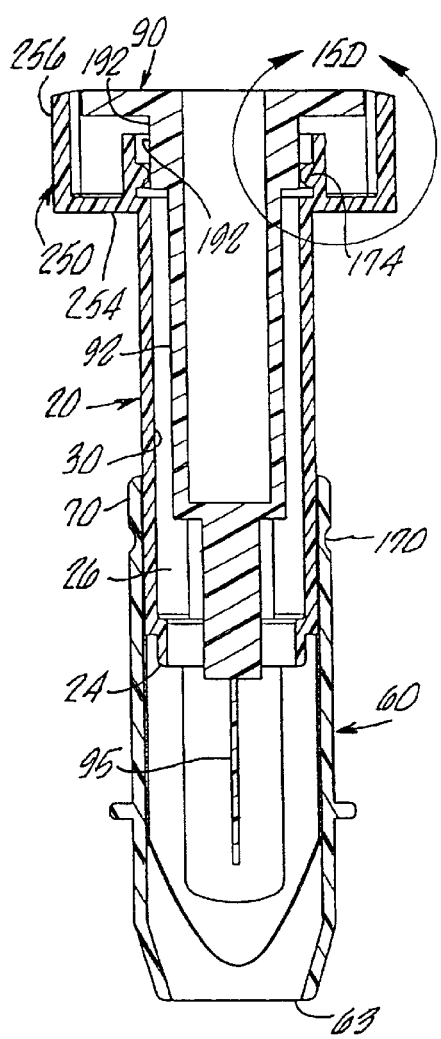
FIG. 15B is a cross-section of the syringe guard of FIG. 15A taken along line B—B.
Figure 15A:
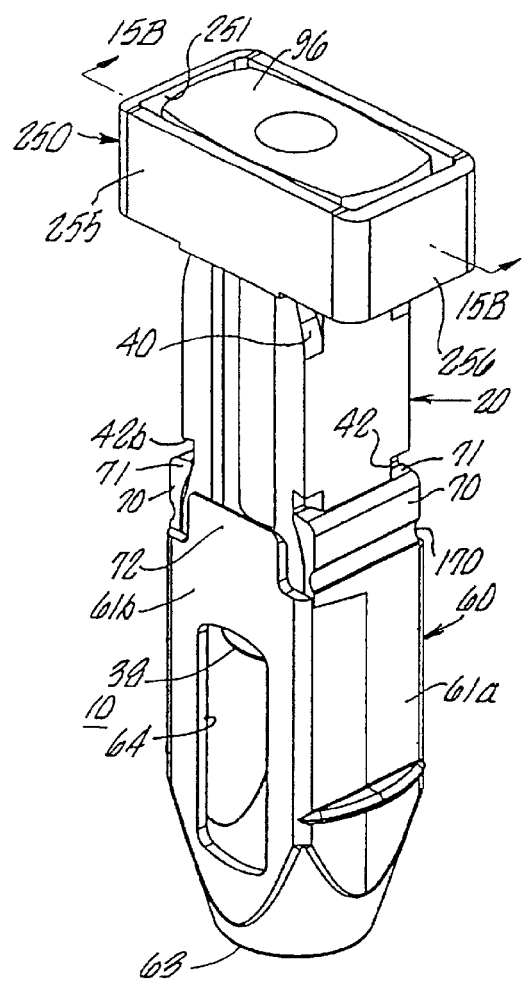
FIG. 15A is a perspective view of a fourth preferred embodiment of a syringe guard holding a pre-filled syringe, with the shield in the guarded position.
Figure 17A:
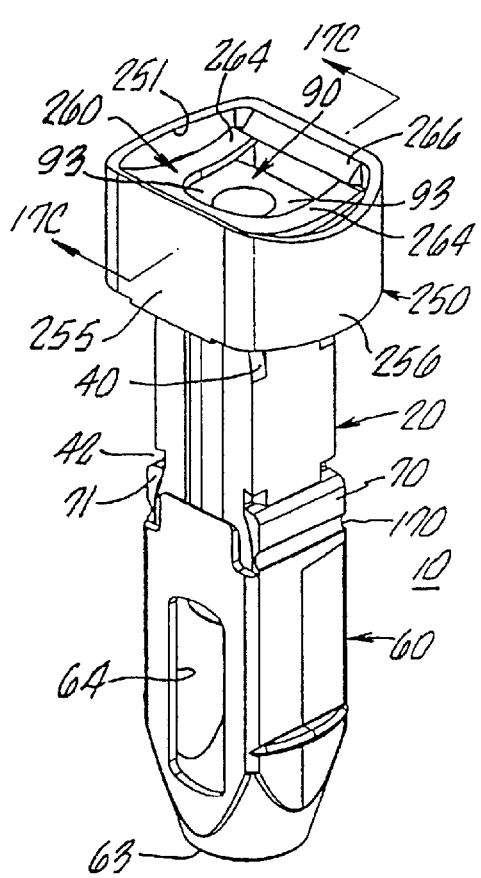
FIG. 17A is a perspective view of a sixth preferred embodiment of a syringe guard holding a pre-filled syringe, with the shield in the guarded position.
Figure 17B:
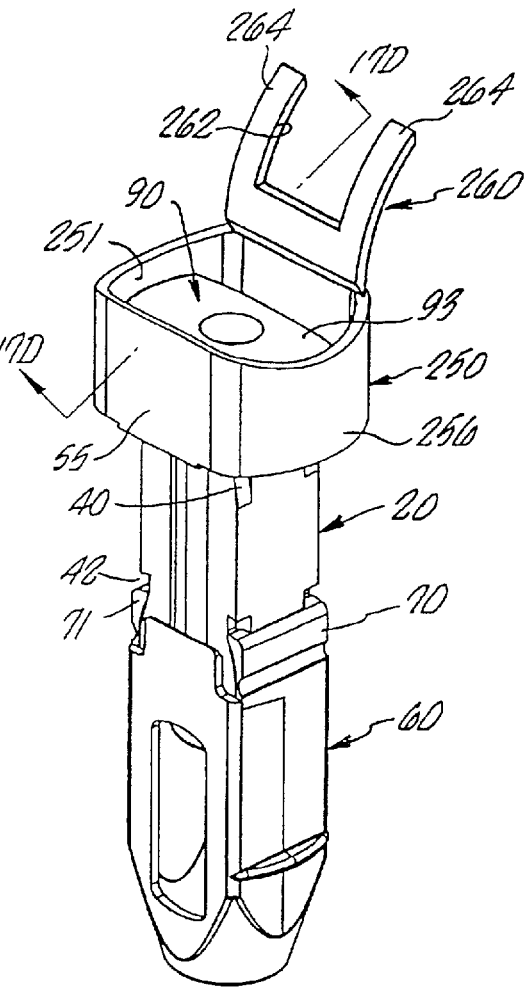
FIG. 17B is a perspective view of the syringe guard of FIG. 17A.

Turning now to FIGS. 14A–14C, a third preferred embodiment of a syringe guard 10 in accordance with the present invention is shown. The syringe guard 10 includes a body 20 and a shield 60 similar to that described above, for receiving a pre-filled syringe 90 including its own plunger (not shown).

The syringe guard 10 also includes a finger grip 150 and a detachable clip or ring 160 for securing the pre-filled syringe 90 to the proximal end 22 of the syringe guard 10. The finger grip 150 includes a pair of wings 152 having a distal surface 154 and a proximal surface 156. Preferably, the wings 152 have a shape substantially similar to the flange 96 on the proximal end 93 of the syringe 90. The clip 160 preferably includes a pair of similarly or identically shaped members, defining a "C" cross-section. The clip 160 includes a cavity 162 having a shape for substantially engaging the finger grip 150 and the flange 96, and includes an aperture 164 for accommodating the plunger (not shown) of the pre-filled syringe 90, the cavity 162 and aperture 164 together defining a plurality of substantially rigid retaining fingers 166.

During use, the pre-filled syringe 90 is introduced into the cavity 26 within the body 20 until the distal edge 96a of the flange 96 abuts the proximal surface 156 of the finger grip 150, and the needle 95 extends beyond the distal end 24 of the body 20. A clip 160 is then directed over the flange 96 and each finger grip wing 152, the retaining fingers 166 substantially engaging the respective proximal and distal surfaces 93b, 154.

Thus, the clips 160 prevent the pre-filled syringe 90 from moving axially (i.e. distally and/or proximally) within the guard 10. In addition, the clips 160 may be sufficiently rigid to prevent the proximal end 94 of the pre-filled syringe 90 from moving substantially laterally during use, thereby possibly eliminating the need for a retaining collar on the proximal end of the body 20. In addition, the apertures 164 on the clips 160 allow the plunger (not shown) to be freely directed distally and/or proximally to dispense medication as desired without substantial interference by the clips 160. In addition, the clips 160 and/or the surfaces 93a, 154 may include cooperating tabs and pockets (not shown) for locking the clips 160, although the clips 160 may be sufficiently retained by friction and/or force fitting them into place.

Alternatively, a detachable ring or clip (not shown) may be provided instead of the pair of clips 160. The ring may be a single hinged piece, with a plurality of retaining fingers or having a recessed perimeter, that may be wrapped around the plunger to engage the finger grip 150 and the flange 96.

Turning now to FIGS. 15A–15D, a fourth embodiment of a syringe guard 10 is shown. Similar to the previous embodiments, the syringe guard 10 includes a body 20 with a finger grip 250, and a shield 60. The finger grip 250 includes an annular shaped collar 172 therein with an annular ring 174 extending radially inward into the cavity 26. Alternatively, the annular collar may be located elsewhere within the body 20, for example in a portion of the cavity 26 distal of the finger grip 250.

Preferably, the annular ring 174 defines a diameter slightly smaller than the outer diameter of the proximal hub 192 of the syringe 90. Alternatively, the annular ring 174 may define a diameter slightly smaller than the barrel 92 itself, or the ring may define an intermittent annular shape (not shown).

A pre-filled syringe 90 may be directed into the cavity 26, the proximal hub 192 engaging the annular ring 174. This creates an interference or frictional fit between the annular ring 174 and the proximal hub 192, thereby substantially retaining the pre-filled syringe 90 within the body 20.

In addition, the finger grip 250 preferably has a substantially rectangular shape corresponding to the generally rectangular shape of the flange 96 on the conventional unit dose pre-filled syringe 90. Thus, the flange 96 may be securely received within a recess 251 within the finger grip 250, thereby preventing the pre-filled syringe 90 from being rotated along its longitudinal axis when encapsulated within the body 20, for example to facilitate observation of a label (not shown) on the barrel 92 through the window 64.

Turning to FIGS. 16A–16D, a fifth preferred embodiment of a syringe guard 10 is shown, that has a body 20, a finger grip 250, and a shield 60. The finger grip 250 includes outer gripping surfaces or walls 256, and lateral surfaces or walls 255 defining a recess 251 for receiving the proximal end 93 of the syringe 90. One or more tabs or detents 258 extend from the finger grip 250 into the recess 251 for engaging the flange 96 to secure the pre-filled syringe 90 within the guard 10.

Preferably, a pair of tabs 258 are integrally formed along the opposite substantially flat walls, for example along outer gripping surfaces s 256, extending into the recess 251 (FIG. 16B). The tabs have ramped proximal surfaces 258a and blunt distal surfaces 258b. Alternatively, a single tab 258 may be provided along a corner of the recess 251 (FIG. 16C), or a pair of tabs 258 may be provided on the lateral surfaces 255 (FIG. 16D).

During use, a pre-filled syringe 90 may be introduced into the body 20 until the flange 96 begins to enter the recess 251 defined by the finger grip 250. The flange 96 engages the ramped proximal surfaces 258a of the tabs 258, forcing the tabs 258 radially outward until the flange 96 substantially enters the recess 251. The tabs 258 then resiliently return radially in, the blunt distal surfaces 258b of the tabs 258 substantially engaging the proximal end 93 of the pre-filled syringe 90, thereby substantially preventing the pre-filled syringe 90 from withdrawing proximally from the body 20. Preferably, the pre-filled syringe 90 includes an enlarged proximal hub (see FIGS. 15B, 15D) which abuts a distal surface within the recess 251, thereby preventing the pre-filled syringe 90 from extending distally through the body 20. In addition, the substantially rectangular shapes of the finger grip 250 and recess 251 require that the pre-filled syringe 90 be inserted in a predetermined orientation, causing a flat edge 96a of the proximal end 93 to abut a wall of the recess to prevent rotational movement of the pre-filled syringe 90. The guard 10 and pre-filled syringe 90 may then be used, similar to the embodiments described above, to deliver medication, and thereafter shield the needle (not shown in FIGS. 16A–16D) with the shield 60.

Alternatively, as shown in FIGS. 17A–17E, the finger grip 250 may include a latch or cover 260 for enclosing the recess 251 once a pre-filled syringe 90 is inserted therein instead of the tabs 258 shown in FIGS. 16A–16D. Preferably, the latch 260 is attached to the finger grip 250 by a hinge 261, although alternatively, the latch 260 may be a separate piece adapted to snap under tabs within the recess (not shown). The latch 260 includes an aperture 262 for accommodating the plunger (not shown) of the pre-filled syringe 90, the aperture being preferably defined by a pair of fingers 264. Preferably, the latch 260 is integrally formed along a wall (e.g. the lateral wall 255) of the finger grip 250 and has a slightly curved cross-section. A tab 266 is preferably integrally formed on and extending inward from the opposite wall (e.g. the opposing lateral wall 55), preferably having a ramped proximal edge 266a and a substantially blunt distal edge 266b. The thickness and/or material of the latch 260 preferably renders the latch 260 semi-rigid, thereby facilitating its insertion into the recess 251 and under the tab 266, as described below.

A pre-filled syringe 90 may be directed into the body 20 until the flange 96 substantially enters the recess 251 and abuts the lower surface 254a. The latch 260 may then be folded along the hinge 261 until it enters the recess 251. The ramped edge 266a forces the tab 266 radially outward, thereby allowing the latch 260 to enter the recess 251. The blunt distal edge 266b then engages the fingers 264, thereby substantially enclosing the recess 251 and preventing the pre-filled syringe 90 from moving proximally from the guard 10 during use.

In a final preferred embodiment, shown in FIGS. 18A–18D, 19 and 20, a syringe guard 10 is provided for receiving relatively small pre-filled syringes 90, for example conventional 0.5 mL capacity pre-filled syringes, which include a rigid nose shield or needle protector cap 97 having a diameter larger than the diameter of the barrel 92 of the pre-filled syringe 90. The syringe guards described above are less preferred for such small pre-filled syringes because such small size pre-filled syringes would require a relatively small guard which may render the devices more difficult or inconvenient to manipulate. Stated differently, a predetermined minimum length and/or cross-section (larger than the length and/or cross-section of the small pre-filled syringe) may be desired for the syringe guard to maximize safe and convenient use of the pre-filled syringe to deliver medication.

Figure 18A:
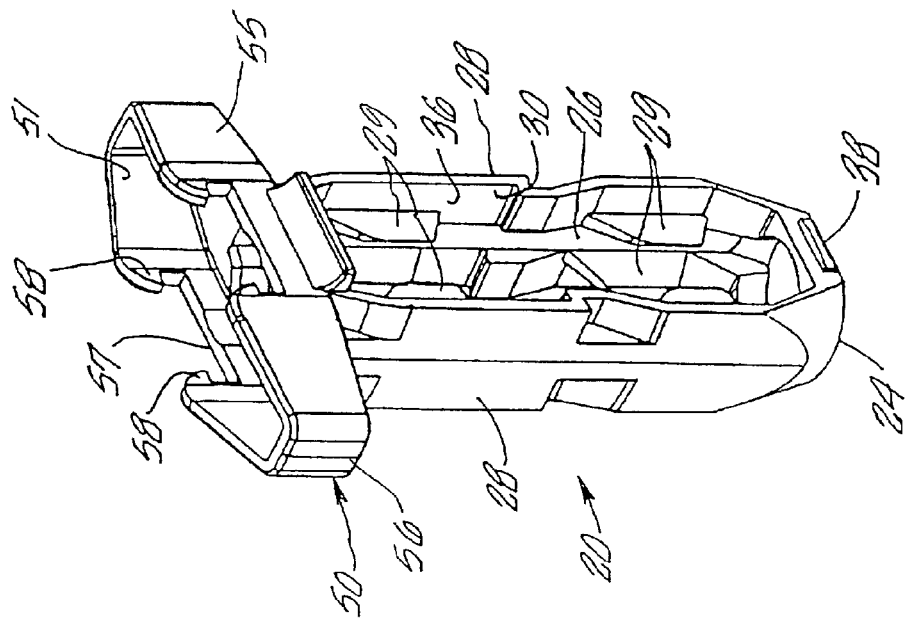
FIG. 18A is a perspective view of a body for a seventh preferred embodiment of a syringe guard for receiving a relatively small pre-filled syringe.
Figure 18B:
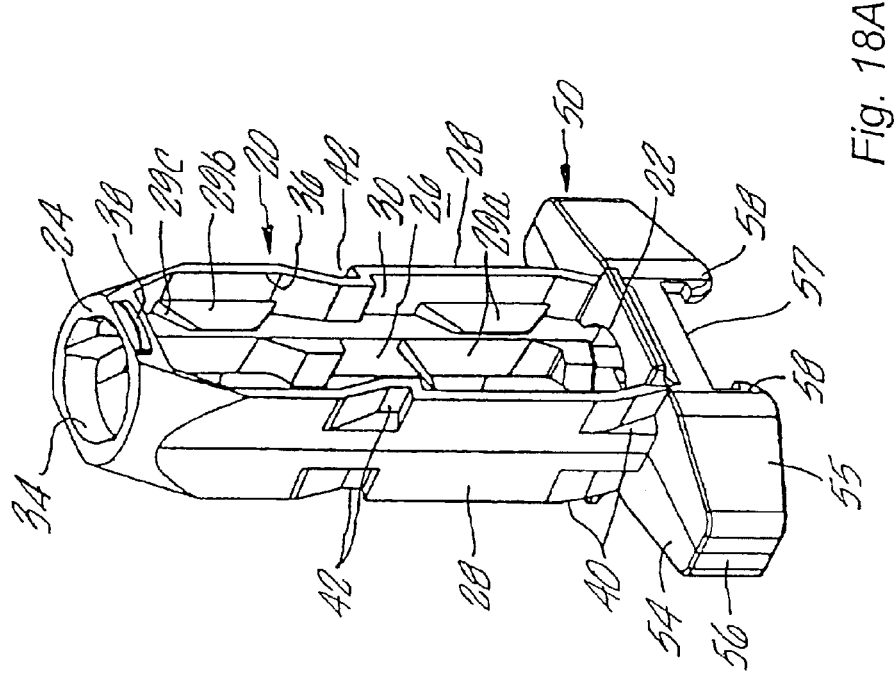
FIG. 18B is another perspective view of the syringe guard body of FIG. 18A.

Generally, the guard 10 includes a body 20 having a locking mechanism in its proximal end for lockably engaging the proximal end 93 and/or flange 96 of the pre-filled syringe 90 received therein, such as the locking mechanisms described above. Preferably, the locking mechanism is sufficiently rigid such that the pre-filled syringe 90 may be substantially retained within the cavity 26 to prevent axial and/or lateral movement without requiring a collar on the distal end 24 of the body 20. For example, the finger grip 50 may include a plurality of locking detents 58 partially defining a slot 57, as shown in FIGS. 18A and 18B. Alternatively,w one or more tabs (not shown) may be provided within the recess 51, for example along the inside of the lateral walls 55, as described above, for engaging the proximal end 93 of the pre-filled syringe 90.

Turning to FIGS. 18A and 18B, the body 20 generally includes a pair of rails 28 defining a cavity 26 for receiving a pre-filled syringe (not shown in FIGS. 18A and 18B), similar to the embodiments described above. The rails 28 may have a "C" cross-section as described above, or may have a substantially flat shape as shown. Preferably, in addition, the inside surfaces 30 of the rails 28 include one or more semi-rigid members or ribs 29 extending from the surfaces 30 into the cavity 26. The ribs 29 are resiliently deflectable to facilitate insertion of the pre-filled syringe 90 and enhance a rigidity characteristic of the body 20. Preferably, the ribs 29 are provided in pairs integrally formed in the rails 28 to at least partially define a diameter or cross-sectional space similar to the diameter of the barrel 92 of the syringe 90 (see FIG. 18D). More preferably, a first set of ribs 29a are provided at or near the distal end 24 of the body 20, and a second set of ribs 29b is provided at or near the proximal end 22. The second or proximal set of ribs 29b may act as lead-in ribs to guide the pre-filled syringe 90 during insertion. Preferably, the lead-in ribs 29b have substantially tapered proximal edges 29c to align the needle cap (not shown).

Figure 18C:
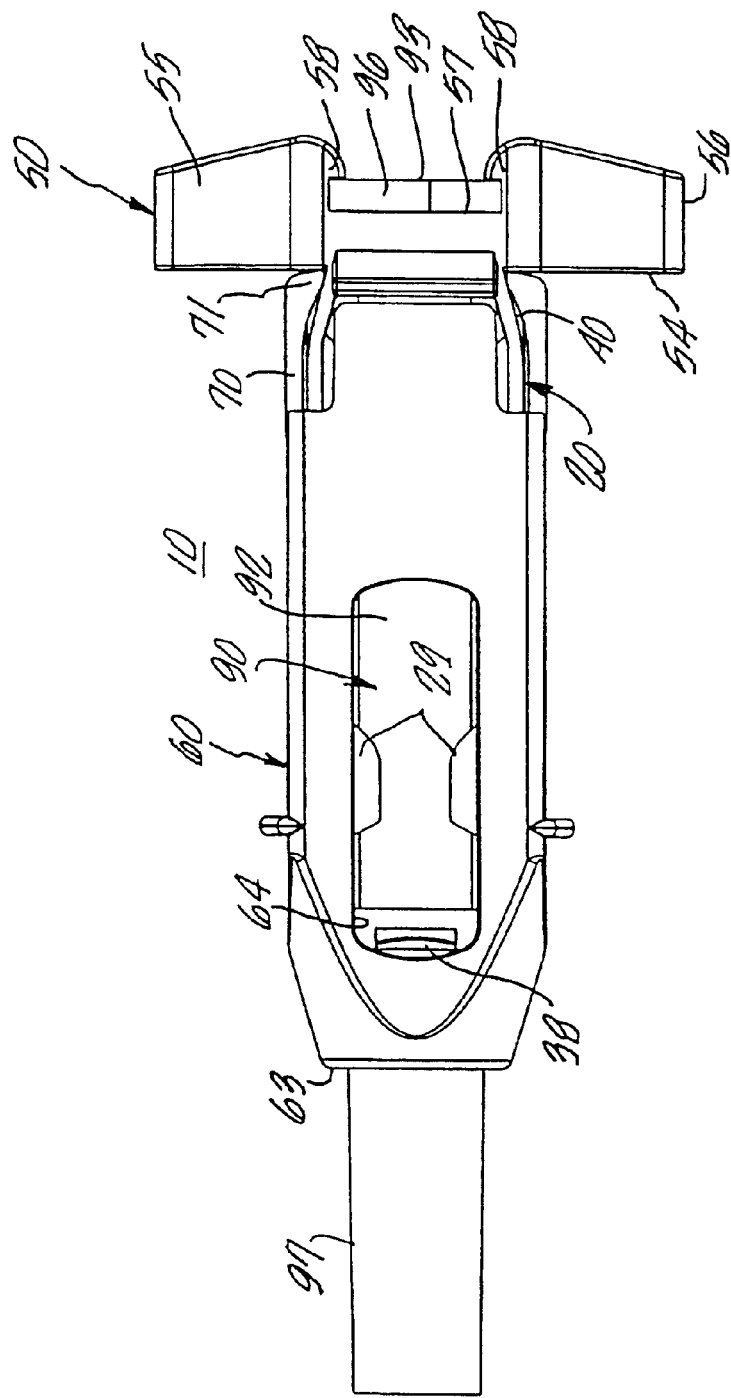
FIG. 18C is a side view of a preferred embodiment of a syringe guard including the body of FIG. 18A, holding a unit dose syringe.
Figure 18D:
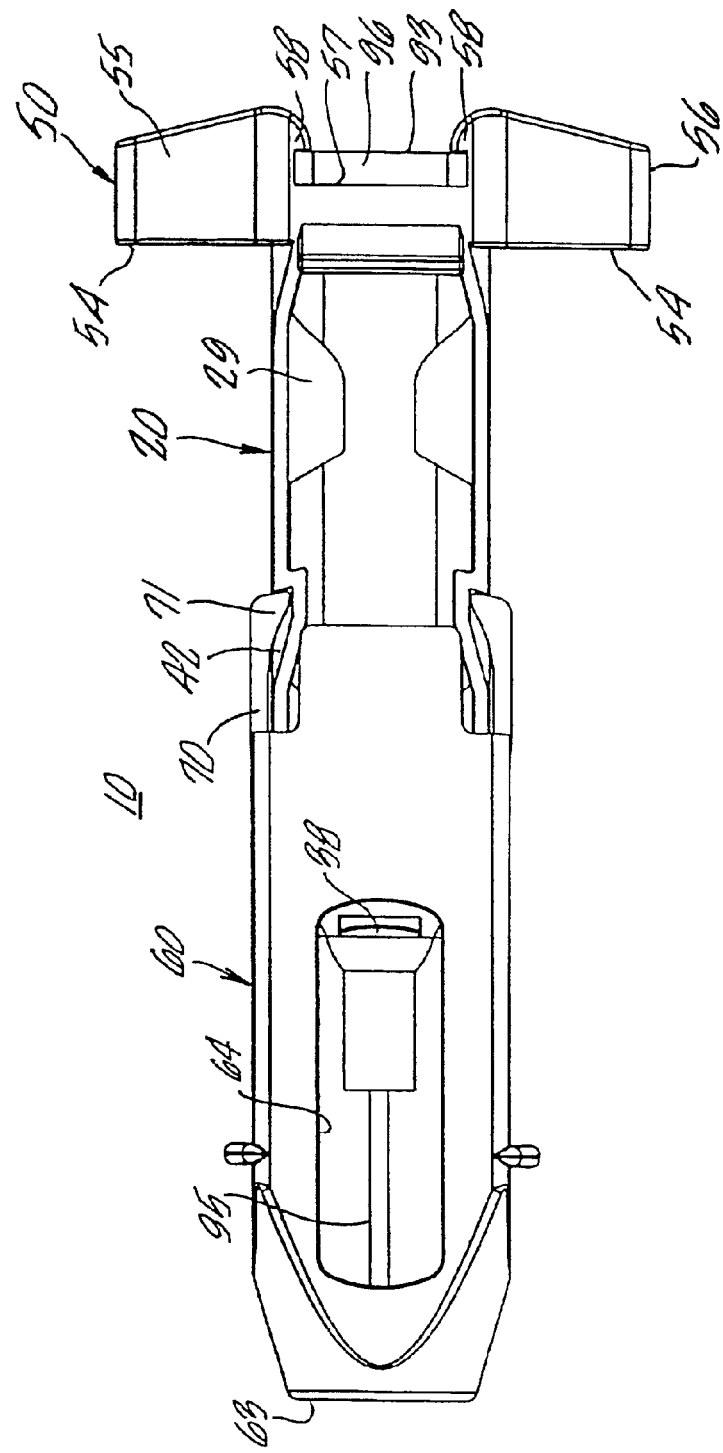
FIG. 18D is a side view of the syringe guard of FIG. 18C, with the shield in the guarded position.

Turning to FIGS. 18C and 18D, a relatively small pre-filled syringe 90 may be inserted into the body 20, the pre-filled syringe 90 including a rigid needle protector cap 97 or similar safety cap having a diameter larger than the barrel 92. When the pre-filled syringe 90 is directed distally into the proximal end 22 of the body 20, the needle protector cap 97 engages the ribs 29 as it enters the cavity 26. Because of the semi-rigid nature of the ribs 29, for example due to the resilience of injection molded plastic, the ribs 29 are deflected outward to accommodate the needle protector cap 97 as it passes distally through the cavity 26.

Alternatively, the fibs 29 may be substantially rigid and the rails 28 themselves may be sufficiently flexible to deform outward as the needle protector cap 97 engages the ribs 29 to allow the cap 97 to pass distally through the cavity 26. In such an embodiment, however, the pre-filled syringe 90 may have to be inserted into the body 20 prior to directing the shield 50 thereon, or the shield 50 may have to be sufficiently flexible and resilient to accommodate the expansion of the rails.

Once the needle protector cap 97 extends beyond the distal end 24 of the body 20, the ribs 29 resiliently return to abut or engage the barrel 92 of the pre-filled syringe 90, thereby preventing substantial lateral movement of the pre-filled syringe 90 within the guard 10 during use.

More preferably, the ribs 29 preferably engage the barrel 92 to enhance the rigidity of the body 20, that is, to prevent the rails 28 from being deflected inward which may release the shield 60 from the guarded position. For example, as can be seen in FIG. 18D, the barrel 92 of the pre-filled syringe 90 has a diameter smaller than the cross-section of the cavity 26 in the body 20. After use of the pre-filled syringe 90, as described previously, the shield 60 is directed distally to the guarded position, wherein the detents 71 engage the pockets 42 to prevent proximal movement of the shield 60 which may expose the used needle 95.

Although the rails 28 are substantially rigid, they may be slightly compressible because of the space between the rails 28 and the barrel 92, which may allow inadvertent release of the detents 71 from the pockets 42 and undesired proximal movement of the shield 60. The ribs 29 provide additional rigidity, for example by substantially engaging the barrel 92, to prevent compression of the rails 28 and thereby improve the safety feature of the shield 60 and cooperating detents 71 and pockets 42.

Figure 19:
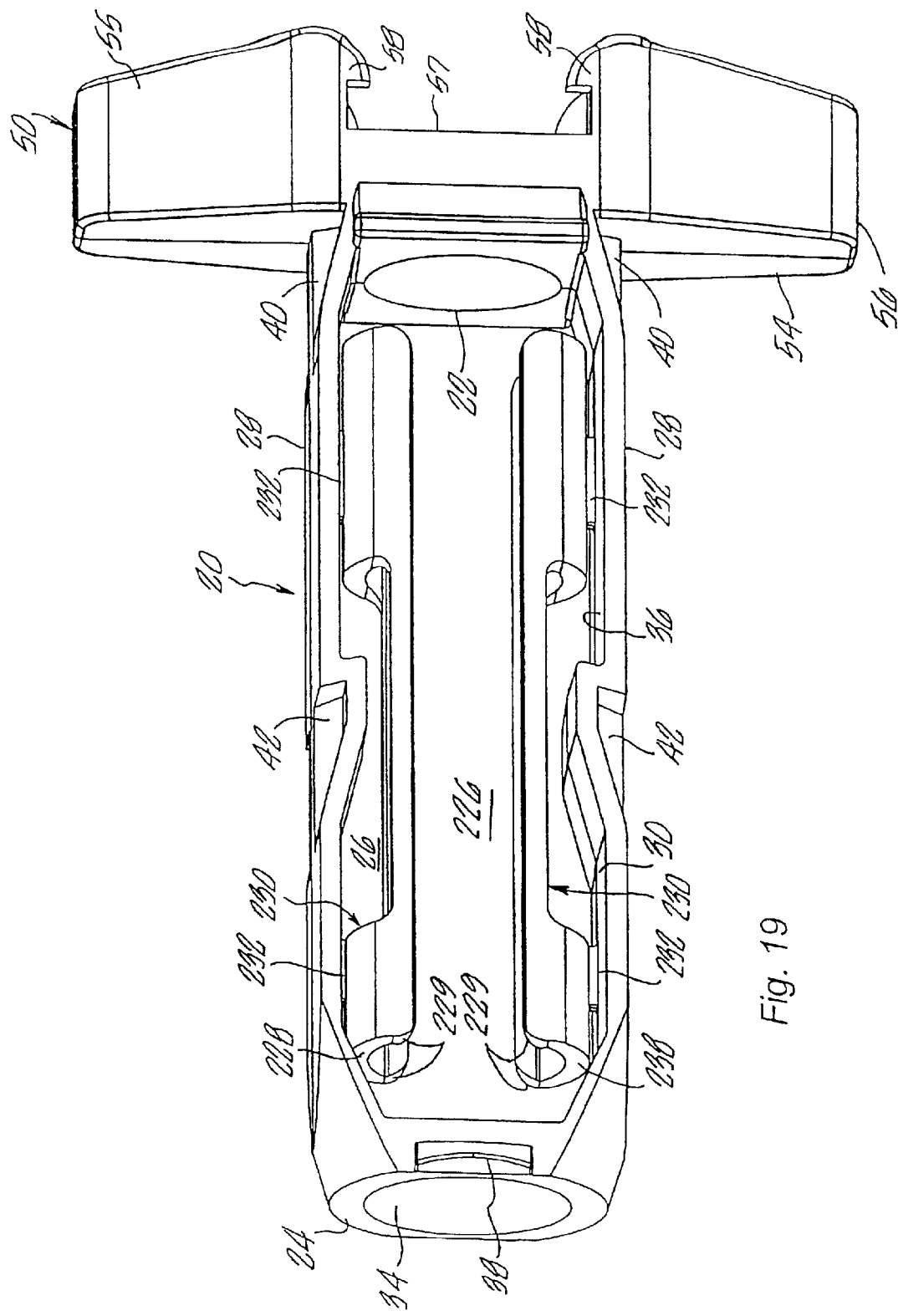
FIG. 19 is a perspective view of an alternative embodiment of the syringe guard body of FIG. 18A.
Figure 20:
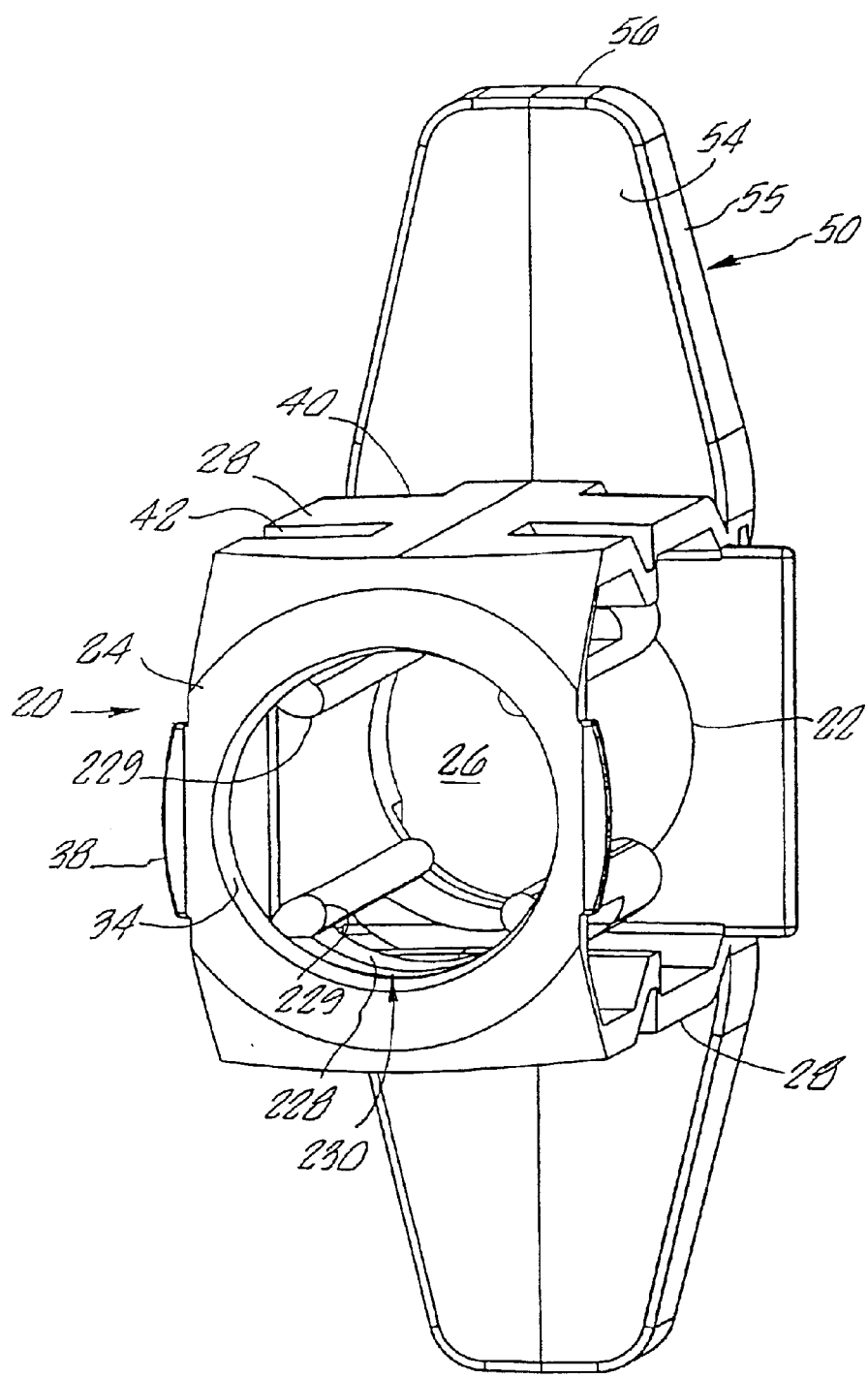
FIG. 20 is a perspective view of another alternative embodiment of the syringe guard body of FIG. 18A.

Alternatively, as shown in FIGS. 19 and 20, the body 20 may include a deflectable cradle or frame 230 for supporting the ribs 229. Preferably, the frame 230 has arms 228 with a curved or semi-circular cross-section defining an inner cavity 226 similar in shape and size to the barrel of the small unit dose pre-filled syringe (not shown) to be received therein. The frame 230 is attached or molded to the rails 28 by one or more support legs or tabs 232. The ribs 229 are then formed along at least a portion of the frame 230, preferably extending between two frames 230 as shown. The ribs 229 may have a tapered (FIG. 19), a rounded (FIG. 20) or other cross-section for engaging the barrel 92 and/or the needle cap 97 of the pre-filled syringe 90.

The deflectable, resilient nature of the frame 230 facilitates the insertion of the pre-filled syringe 90 being received in the body 20. The arms 228 on the frame 230 may be deflected outward to accommodate the needle protector cap 97, but resiliently return to engage the barrel 92 with the ribs 229, thereby providing additional rigidity for the rails 28, as described above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A guard for a syringe comprising a proximal end and a distal end, a lip on the proximal end, and a needle extending from the distal end, the guard comprising:

a body comprising a cavity for receiving the syringe axially therein through an open proximal end of the body, and comprising an open distal end;

one or more lateral surfaces on the proximal end of the body defining a recess for receiving the proximal end of the syringe therein, the lateral surfaces comprising a locking mechanism for substantially permanently engaging the lip on the proximal end of the syringe received in the cavity;

a shield slidably attached to the body, and having open proximal and distal ends, the shield being slidable between an unguarded and a guarded position, the needle on the syringe extending through the open distal end in the unguarded position and being covered by the shield in the guarded position; and cooperating detents on the shield and body for holding the shield in the unguarded and guarded positions, wherein the locking mechanism comprises locking detents in the lateral surfaces for engaging the proximal end of the syringe received in the cavity, thereby substantially permanently locking the syringe in the body.

2. The guard of claim 1, wherein the locking detents have tapered proximal edges and blunt distal edges for substantially permanently receiving the lip on the syringe thereunder.

3. The guard of claim 1, wherein the locking detents define slots for receiving the lip therein, thereby preventing the syringe from being removed proximally from the body.

4. A syringe comprising:

a syringe holding medication comprising proximal and distal ends, the syringe comprising a needle extending from the distal end and a lip on the proximal end;

a body comprising a cavity for receiving the syringe axially therein through an open proximal end of the body, and comprising an open distal end;

one or more lateral surfaces on the proximal end of the body defining a recess for receiving the proximal ends of the syringe therein, the lateral surfaces comprising a locking mechanism for engaging the lip to substantially permanently encapsulate the syringe in the body;

a shield slidably attached to the body, and having open proximal and distal ends, the shield being slidable between an unguarded and a guarded position, thereby uncovering and covering, respectively, the needle on the syringe; and cooperating detents on the shield and body for holding the shield in the guarded and unguarded positions, wherein the locking mechanism comprises locking detents in the lateral surfaces for engaging the proximal end of the syringe received in the cavity, thereby substantially permanently locking the syringe in the body.

5. The guard of claim 4, wherein the locking detents have tapered proximal edges and blunt distal edges for substantially permanently receiving the lip on the syringe thereunder.

6. The guard of claim 4, wherein the locking detents define slots for receiving the lip therein, thereby preventing the syringe from being removed proximally from the body.

7. A guard for a syringe comprising a proximal end and a distal end, a lip on the proximal end, and a needle extending from the distal end, the guard comprising:

a body for receiving the syringe axially through an open proximal end of the body, and comprising an open distal end, the body comprising one or more lateral surfaces defining a recess for receiving the proximal end of the syringe therein, the one or more lateral surfaces comprising one or more slots for receiving at least a portion of the lip of the syringe therein for substantially permanently locking the syringe to the body;

a shield slidably attached to the body, and having open proximal and distal ends, the shield being slidable between an unguarded and a guarded position, the needle on the syringe extending through the open distal end in the unguarded position and being covered by the shield in the guarded position; and cooperating detents on the shield and body for holding the shield in the unguarded and guarded positions.

8. The guard of claim 7, further comprising a finger hold on the shield.

* * * * *

UNITED STATES PATENT AND TRADEMARK OFFICE
CERTIFICATE OF CORRECTION

PATENT NO. : 7,041,085 B2 Page 1 of 1
APPLICATION NO. : 10/023587
DATED : May 9, 2006
INVENTOR(S) : Anthony R. Perez, John R. Firth and David W. Mitchell It is certified that error appears in the above-identified patent and that said Letters Patent is hereby corrected as shown below:

Column 21, line 38, Claim 4, change "ends" to -- end --.

Signed and Sealed this

Sixth Day of May, 2008

JON W. DUDAS
*Director of the United States Patent and Trademark Office*